United States Patent [19]

Yamashita et al.

[11] Patent Number: 5,302,762
[45] Date of Patent: Apr. 12, 1994

[54] METHOD FOR HYDRATING A CYCLOOLEFIN

[75] Inventors: Kunihiko Yamashita, Kurashiki; Hideaki Obana, Kamakura; Tadashi Kai, Machida, all of Japan

[73] Assignee: Asahi Kasei Kogyo Kabushiki Kaisha, Osaka, Japan

[21] Appl. No.: 32,220

[22] Filed: Mar. 17, 1993

[51] Int. Cl.⁵ ............................................. C07C 29/04
[52] U.S. Cl. ..................................... 568/895; 568/835
[58] Field of Search ................ 568/835, 895; 422/224, 422/228, 227, 225, 188, 189

[56] References Cited

U.S. PATENT DOCUMENTS

| | | | |
|---|---|---|---|
| 3,994,983 | 11/1976 | Webers et al. | 568/895 |
| 4,558,846 | 5/1986 | Mitsui et al. | 568/835 |
| 4,661,639 | 4/1987 | Tojo et al. | 568/835 |

FOREIGN PATENT DOCUMENTS

| | | | |
|---|---|---|---|
| 0341163 | 11/1989 | European Pat. Off. | 568/835 |
| 2275428 | 1/1976 | France | 568/895 |
| 43-16125 | 7/1968 | Japan . | |
| 60-248632 | 12/1985 | Japan . | |
| 60-248633 | 12/1985 | Japan . | |
| 60-248635 | 4/1986 | Japan . | |
| 61-68319 | 8/1986 | Japan . | |
| 61-180735 | 8/1986 | Japan . | |
| 61-221141 | 10/1986 | Japan . | |
| 62-36017 | 2/1987 | Japan . | |
| 63-154633 | 6/1988 | Japan . | |
| 63-315512 | 12/1988 | Japan . | |
| 1-180835 | 7/1989 | Japan . | |
| 1-190644 | 7/1989 | Japan . | |
| 1-192717 | 8/1989 | Japan . | |
| 4-41131 | 7/1992 | Japan . | |
| 60-248634 | 12/1985 | United Kingdom . | |

OTHER PUBLICATIONS

Ullman's Encyclopedia of Industrial Chemistry, vol. B4, 1992.
38-15619, Aug. 1963, Japanese Patent.
44-26656, Nov. 1963, Japanese Patent.

*Primary Examiner*—Werren B. Lone
*Attorney, Agent, or Firm*—Pennie & Edmonds

[57] ABSTRACT

Disclosed is a method for hydrating a cycloolefin, in which the hydration is conducted in a reaction system comprising a continuous aqueous phase including water and a crystalline aluminosilicate catalyst suspended therein and an oil phase including a cycloolefin, while dispersing the oil phase as globules having a specific diameter. By the method of the present invention, not only can a cyclic alcohol be produced at high selectivity and in high yield, but the activity of the catalyst can also be stably maintained at a high level for a prolonged period of time, and the produced cyclic alcohol can be readily separated.

25 Claims, 10 Drawing Sheets

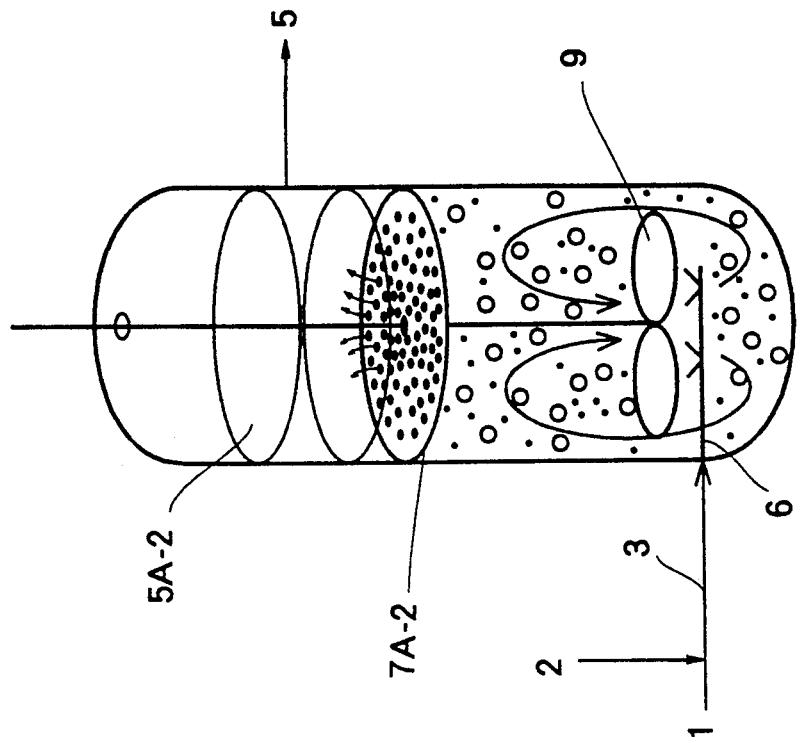
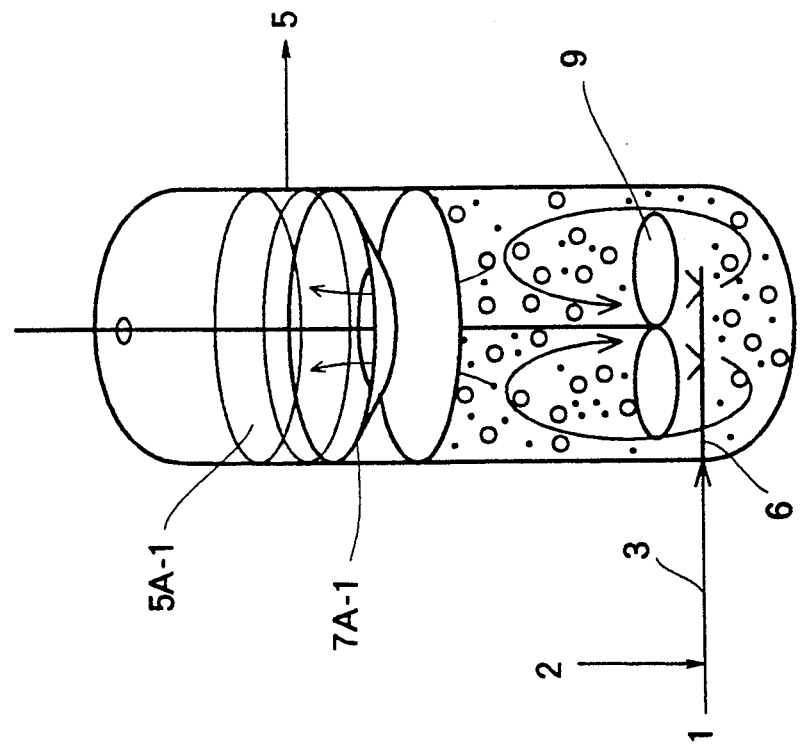

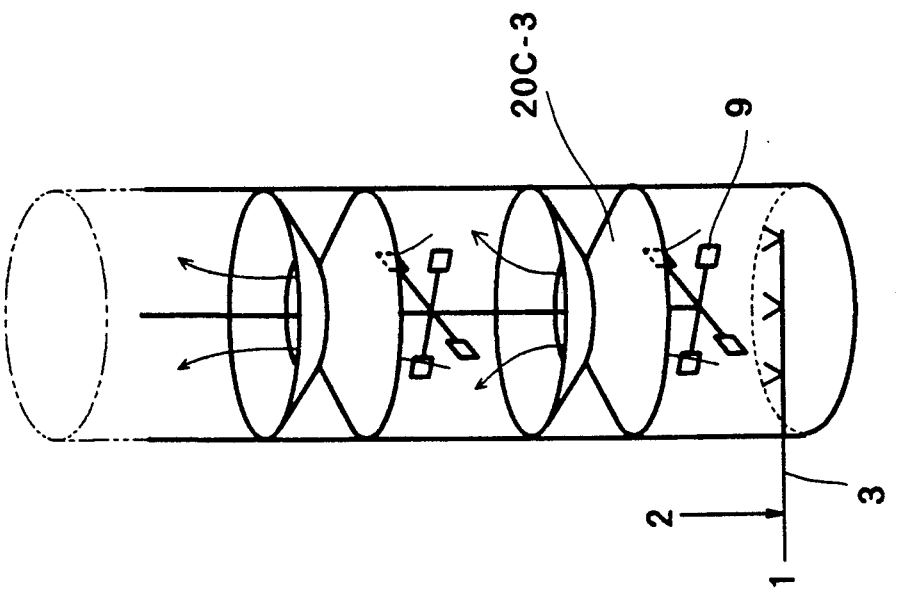
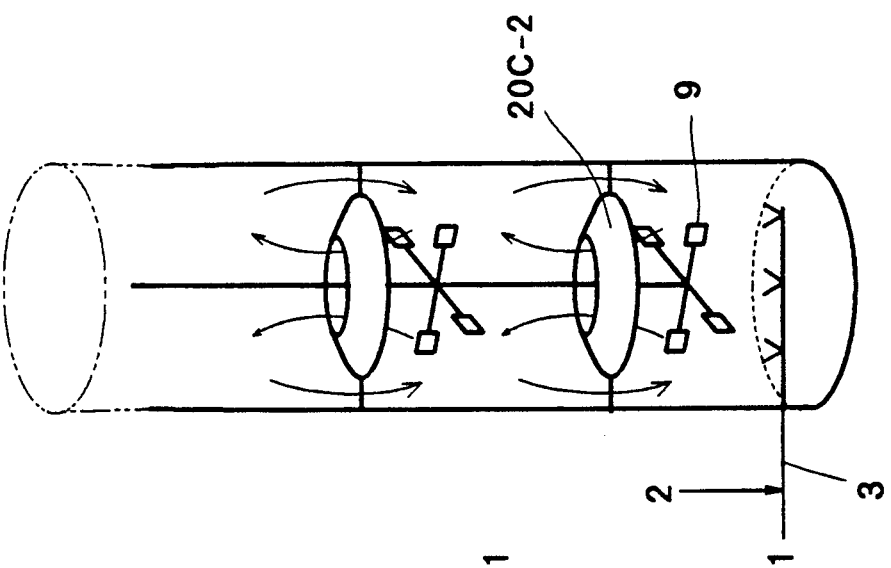
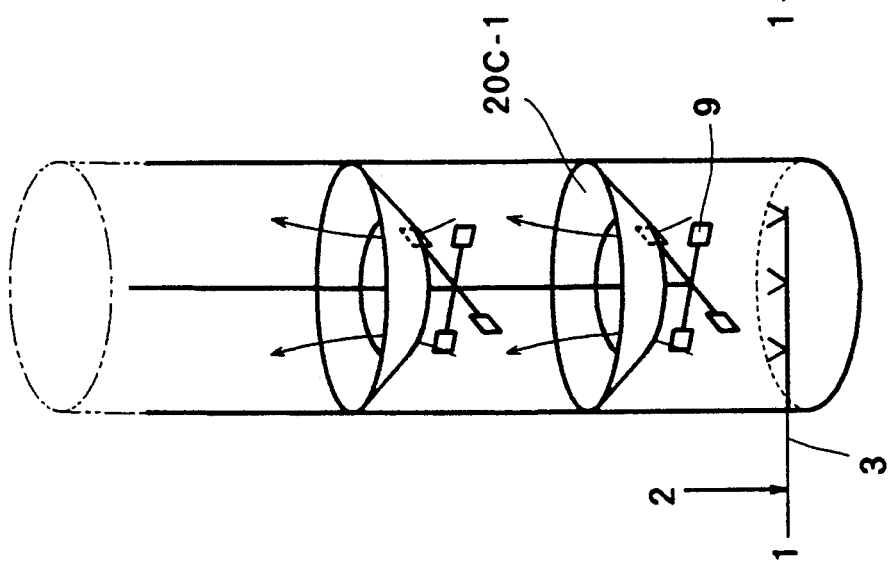

METHOD FOR HYDRATING A CYCLOOLEFIN

BACKGROUND OF THE INVENTION

1. Field of The Invention

The present invention relates to a method for hydrating a cycloolefin to produce a cyclic alcohol. More particularly, the present invention is concerned with a method for hydrating a cycloolefin, in which the hydration is conducted in a reaction system comprising a continuous aqueous phase including water and a crystalline aluminosilicate catalyst suspended therein and an oil phase including a cycloolefin, while dispersing the oil phase as globules having a specific diameter In the method of the present invention, not only can a cyclic alcohol be produced at high selectivity and in high yield, but the activity of the catalyst can also be stably maintained at a high level for a prolonged period of time, and the produced cyclic alcohol can be readily separated.

2. Discussion of Related Art

Various methods for hydrating a cycloolefin by reacting the same with water to produce a cyclic alcohol have been proposed, which include for example, a method in which indirect or direct hydration of a cycloolefin is carried out using a mineral acid, such as sulfuric acid, as a homogeneous catalyst, and a method in which the hydration is carried out using an aromatic sulfonic acid as a homogeneous catalyst (see Japanese Patent Application Publication Specification No. 43-16125/1968). In Example 2 of this published specification, 200 g of an oil phase comprised of a mixture of cyclohexene and cyclohexane is reacted at 90° C. for 12 hours with 160 g of an aqueous phase comprised of water containing p-toluenesulfonic acid. After completion of the reaction, the aqueous phase is separated from the oil phase, and 200 g of water is added to the aqueous phase and subjected to steam distillation while heating. By the steam distillation, cyclohexanol is distilled off to obtain the same. This procedure has drawbacks in that the separation of cyclohexanol as a reaction product from the aqueous phase is not only time-consuming but also disadvantageously causes a large energy consumption.

As a method for coping with the above-mentioned drawbacks of the method using a homogeneous catalyst, a method has been proposed in which a solid catalyst, such as an ion exchange resin, is used (see Japanese Patent Application Publication Specification No. 38-5619/1963 and Japanese Patent Application Publication Specification No. 44-26656/1969). However, this method also has a drawback in that the activity of the catalyst cannot be maintained for a long time because the ion exchange resin is likely to suffer from pulverization due to a mechanical degradation of the resin and because the heat resistance of the resin is unsatisfactory.

As another solid catalyst, the use of a crystalline aluminosilicate has been proposed, which is believed to be advantageous for commercial production of a cyclic alcohol because this catalyst is insoluble in water and excellent in mechanical strength and heat resistance properties. Japanese Patent Application Laid-Open Specification No. 60-104028/1985 (corresponding to U.S. Pat. No. 4,588,846) discloses examples in which a pulverized crystalline aluminosilicate is used as a solid catalyst In particular, this published specification discloses a method, in which water, an aluminosilicate catalyst and cyclohexene as a feedstock are charged in an autoclave reactor equipped with an agitator, and heated at 50° to 250° C. for 15 minutes to 4 hours, followed by isolation of cyclohexanol as a reaction product from an oil phase. The reaction system used in this method is a three-phase heterogeneous system comprised of an oil phase mainly including cyclohexene, an aqueous phase mainly including water and a solid phase including the aluminosilicate catalyst suspended in the aqueous phase. In the conventional method using such a reaction system, problems have often been encountered. Illustratively stated, the conventional method has problems in that when the mixing of the oil phase with the aqueous phase is insufficient, the activity of the aluminosilicate catalyst in the reaction system cannot be fully exerted and therefore the yield becomes unfavorably low. On the other hand, when the mixing of the oil phase with the aqueous phase is too vigorous, an unfavorably long period of time is required in the separation of the oil phase containing a produced cyclic alcohol from the aqueous phase in a stationary zone provided for the separation after completion of the hydration reaction The period of time required for the separation can be shortened by the installation of a large stationary zone, which is, however, unfavorable from the viewpoint of productivity. Further, depending upon the properties of the aluminosilicate catalyst employed and the impurities contained in the catalyst, water and cyclohexene, the reaction system suffers from emulsification to thereby cause the separation of an oil phase including produced cyclohexanol from the aqueous phase to be difficult and cause the catalyst to be leaked into cyclohexanol as a reaction product. Thus, a stable, continuous reaction is difficult to maintain. For breaking such an emulsion, a countermeasure may be conceived which comprises subjecting a reaction product, being formed, containing the aluminosilicate catalyst to centrifugation during the reaction. However, in this countermeasure, it is likely that the centrifuge used is hindered by the adhesion of catalyst deposits, and that the catalyst is disintegrated to thereby hamper the recovery of the catalyst. Accordingly, the above-mentioned countermeasure is not practicable. Further, once emulsification occurs, even if the emulsion is broken to separate the catalyst, the activity loss of the separated catalyst is disadvantageously large as compared to that of the catalyst recovered through the separation of the catalyst from a reaction product containing the catalyst in a stationary zone. Hence, a cycloolefin hydration method free from the emulsification problem has been desired in the art.

Therefore, the conventional methods for hydrating a cycloolefin to produce a cyclic alcohol have been unsatisfactory not only in that the desired cyclic alcohol cannot be obtained in consistently high yield, but also in that the separation of the oil phase containing a produced cyclic alcohol from the aqueous phase after the hydration reaction cannot be efficiently conducted.

SUMMARY OF THE INVENTION

With a view toward developing a method for hydrating a cycloolefin which is free from the above-mentioned drawbacks inevitably accompanying the conventional methods, the present inventors have conducted extensive and intensive studies. As a result, it has unexpectedly been found that this goal can be attained by a method in which the hydration is conducted in a reaction system comprising a continuous aqueous phase including water and an aluminosilicate catalyst suspended therein and a hydrophobic or oil phase containing a cycloolefin while dispersing the oil phase in the continuous aqueous phase as globules having a specific diameter. Based on this unexpected finding, the present invention has been completed.

It is, therefore, an object of the present invention to provide a method for hydrating a cycloolefin, which can advantageously be used for producing a cyclic alcohol on a commercial scale, and in which not only can a cyclic alcohol be produced at high selectivity and in high yield, but the activity of the catalyst can also be stably maintained at a high level for a prolonged period of time, and the separation of a produced cyclic alcohol is also easy.

The foregoing and other objects, features and advantages of the present invention will become apparent from the following detailed description and appended claims taken in connection with the accompanying drawings.

BRIEF DESCRIPTION OF THE DRAWINGS

In the drawings:

FIGS. 6 (a) and 6(b) are diagrammatic views showing various types of partition members, such as a doughnut type plate [FIG. 6 (a)] and a perforated plate [FIG. 6 (b)], which can be used in a reactor of the type shown in FIG. 5;

In FIGS. 1 through 9, like parts and portions are designated by like numerals. Vacant circles in FIGS. 1 through 8 indicate oil globules, and dots indicate a hydration catalyst.

DETAILED DESCRIPTION OF THE INVENTION

Figure 1:
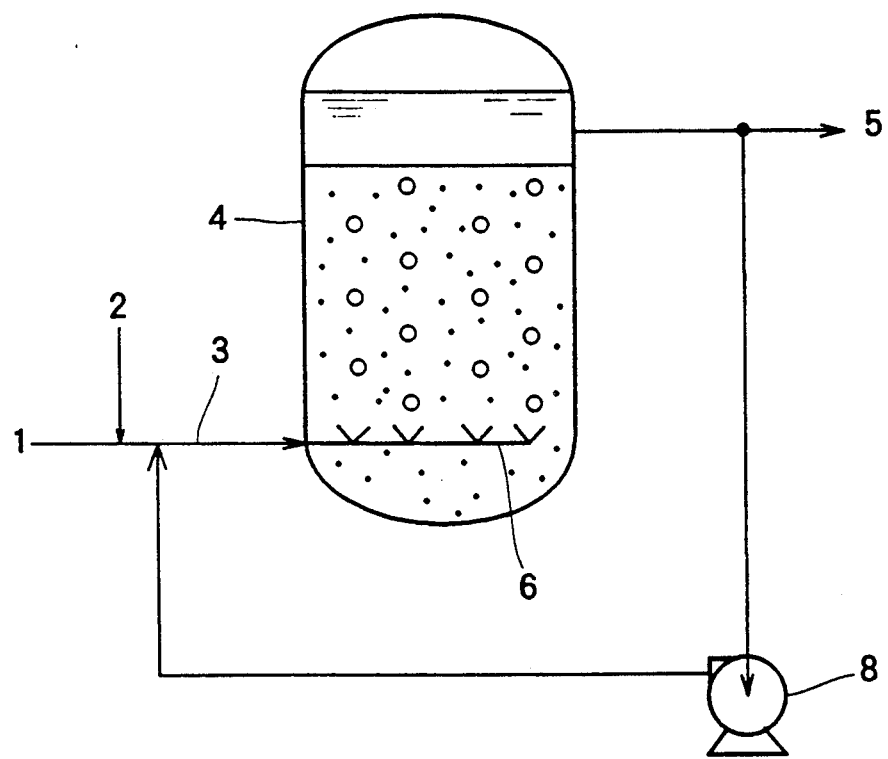
FIG. 1 is a diagrammatic view illustrating one mode of the method of the present invention, in which a reactor having a disperser head connected to a feed pipe is shown in cross-section to show the interior thereof.

Essentially, according to the present invention, there is provided a method for hydrating a cycloolefin to produce a cyclic alcohol, comprising reacting a cycloolefin with water in the presence of a crystalline aluminosilicate catalyst in a reaction system comprising:

a continuous aqueous phase including water and the crystalline aluminosilicate catalyst suspended therein; and an oil phase including the cycloolefin, while dispersing the oil phase in the continuous aqueous phase as globules having an average diameter (as hereinafter defined) of between about 0.05 and about 30 mm.

The reaction mechanism involved in the method of the present invention is explained below, taking as an example the case in which cyclohexene is used as the cycloolefin. In the reaction system, cyclohexene included in the oil phase is caused to be diffused and dissolved in the continuous aqueous phase having a hydration catalyst suspended therein through an oil phase-aqueous phase interface. The cyclohexene which has been diffused and dissolved in the continuous aqueous phase is adsorbed onto a number of active sites on the surface of the hydration catalyst, so that the cyclohexane is caused to be reacted with the water at the active sites, to thereby produce cyclohexanol. The produced cyclohexanol is released from the catalyst and then diffused and dissolved into the continuous aqueous phase. The cyclohexanol is then transferred from the continuous aqueous phase to the oil phase through the oil phase-aqueous phase interface. The cyclohexanol is isolated from the oil phase by for example, distillation. As is apparent from the above, in the reaction system of the method of the present invention, mass transfers occur.

The terminology "oil phase" used herein means a phase comprised of a cycloolefin and a cyclic alcohol, which may include water dissolved therein. The terminology "aqueous phase" used herein means a phase comprised of water and a crystalline aluminosilicate catalyst suspended therein, which may include dissolved cycloolefin and cyclic alcohol.

The hydration reaction of a cycloolefin such as cyclohexene is a thermodynamically-controlled equilibrium reaction, and at temperatures of from 50° to 250° C., the hydration reaction proceeds according to the formula:

$$K_p = \frac{C_1}{C_2 \cdot C_3} \quad (1)$$

wherein:

$K_p$ represents thermodynamic equilibrium constant;
$C_1$ represents the molar concentration of cyclohexanol in the aqueous phase;
$C_2$ represents the molar concentration of cyclohexene in the aqueous phase; and
$C_3$ represents the molar concentration of water in the aqueous phase.

The value of the thermodynamic equilibrium constant $K_p$ is in the order of $10^{-3}$, so that when cyclohexene is reacted in a reaction system comprised of water in which no oil phase is present and a catalyst, the yield of cyclohexanol is extremely small. However, when an oil phase is present as in the reaction system employed in the present invention, the distribution equilibrium of cyclohexanol between the oil phase and the aqueous phase is markedly inclined toward the oil phase (for example, the cyclohexanol concentration of the oil phase is from 1 to 30% by weight, whereas the cyclohexanol concentration of the aqueous phase is from 0.1 to 5% by weight), so that due to the higher concentration of cyclohexanol in the oil phase, cyclohexanol can be obtained in high yield from the oil phase. This suggests that the presence of the oil phase is indispensable for obtaining the cyclic alcohol in high yield.

In the heterogeneous reaction, mass transfers, such as the diffusion of reactants and reaction products to a phase interface and through a phase interface, affect the reaction rate. The reaction rate is governed by the product of the overall reaction rate constant, multiplied by the reactant concentration The overall reaction rate constant is governed by the mass transfer coefficient and the reaction rate constant on a catalyst.

The present inventors have studied experimental data taken with an autoclave reactor equipped with an agitator, regarding reaction rate. As a result, they have found that although the reaction rate on a catalyst is relatively large, the rate of mass transfer, including the dissolution of cyclohexene from the oil phase into the aqueous phase and the extraction of produced cyclohexanol from the aqueous phase into the oil phase, is likely to become lower than the reaction rate on a catalyst, depending upon the conditions of the reaction system, thereby causing the overall reaction rate to be decreased.

In particular, when the agitation is poor, it is likely that the oil phase is caused to be separated to form an oil phase on an aqueous phase, thereby forming two layers. In this case, the interfacial area of the oil phase and the aqueous phase becomes unsatisfactorily small, which is causative of being mass transfer rate-limiting, so that the overall reaction rate becomes extremely small.

The overall mass transfer rate at the interface between the oil phase and the aqueous phase is represented by the product (KL·a) of boundary film mass transfer coefficient (KL), multiplied by the interfacial area per volume (a). The boundary film mass transfer coefficient (KL) depends upon the properties (such as, diffusion coefficient, viscosity and density) of the oil phase and the aqueous phase, the velocity of oil globules relative to the continuous aqueous phase, and the size of the oil globules On the other hand, the interfacial area (a) is represented by the product of the number of oil globules, multiplied by the specific area of oil globule. An interfacial area suitable for mass transfer is ensured by the presence of a large number of fine oil globules. Accordingly, the smaller the size of oil globule, the better the results. However, when the size of the oil globule is too small, a prolonged period of time is required for unification or coalescence of the oil globules into a stationary zone for the separation of the oil phase from the aqueous phase after completion of the reaction, so that the area of the stationary zone needs to be unfavorably large. Moreover, when impurities which function as a surfactant are present in cyclohexene feedstock, oil globules that are too fine have less tendency for unification, so that the reaction system becomes emulsified to cause the separation of the oil phase to be extremely difficult.

In the present invention, the time required for separating the reaction system in a stationary zone into the oil phase and the aqueous phase is measured by the following method. Predetermined amounts of cyclohexene and water including an aluminosilicate catalyst suspended therein are charged into a 4-liter stainless steel autoclave reactor having a peep window in the wall thereof and the hydration reaction is started by supplying cyclohexene and water while agitating. When the supply and the agitation are stopped, the movement of the reaction system caused by the agitation stops, and the oil globules dispersed in the aqueous phase begin to spontaneously ascend and these globules are unified in the upper portion of the reaction system in the reactor, thereby gradually forming a continuous oil phase above the continuous aqueous phase. The level of the lower surface of the continuous oil phase continues to descend until the oil globules have been completely unified and the reaction system is clearly separated into the continuous oil phase and the continuous aqueous phase devoid of oil globules (at this time, the level of the lower surface of the continuous oil phase, i.e., the level of the interface between the continuous oil and aqueous phases becomes stable). The time between the moment at which the movement of the reaction system caused by the agitation stops and the moment at which the level of the lower surface of the continuous oil phase becomes stable, is defined as the time for separating the oil phase from the aqueous phase (i.e., the oil-water separating time). In the method of the present invention, when the volume of the reaction system is, for example, 4 liters, the oil-water separating time is generally between about 2 and about 30 seconds. When the volume of the reaction system is large, it takes a longer time for the oil globules to ascend to form a continuous oil phase, so that the oil-water separating time is prolonged.

The velocity of the above-mentioned lowering of the lower surface of the continuous oil phase is an important factor in designing the stationary zone, and is designated as $V_o$. Cyclohexene as an oil phase is preferably fed into the reactor at an in-column velocity, $V_e$, which is smaller than $V_o$.

When the unification of oil globules is not a rate-limiting step in the oil-water separation, the velocity of the lowering of the lower surface of the continuous oil phase can be determined as follows. First, the terminal velocity in the Stokes' law region, $U_m$, of oil globules is obtained according to the formula (2) below, and then the above-mentioned lowering velocity, $V_o$, is calculated according to the formula (3) showing the relationship between the ascending velocity, $U_m$, of oil globules and the volume ratio, $\epsilon$, of oil globules to the aqueous phase.

$$U_m = \frac{g(\rho_c - \rho_d) d_p^2}{18\mu} \quad (2)$$

wherein:
$U_m$ represents the ascending velocity of the oil globules;
g represents gravity;
$\rho_c$ represents the density of the continuous oil phase;
$\rho_d$ represents the density of the oil globules;
$\rho_p$ represents the diameter of the oil globules; and
$\mu$ represents the viscosity of the reaction system.

$$V_o = \epsilon \cdot U_m \quad (3)$$

wherein:

$V_o$ represents the velocity of the lowering of the lower surface of the continuous oil phase;

$\epsilon$ represents the volume ratio of the oil globules to the aqueous phase; and $U_m$ is as defined above.

As seen from these formulae, the oil-water separating time can be reduced not only by increasing the size of oil globule but also by increasing the temperature of the reaction system to thereby lower the viscosity of the reaction system and accordingly increase the ascending velocity of oil globules. On the other hand, when the oil globules are so fine as to cause the reaction system to suffer from emulsification, the unification of oil globules at an upper portion of the reactor is prevented to thereby cause the formation of a continuous oil phase to be difficult. In this case, the formulae (2) and (3) do not apply.

As apparent from the above, the oil globules should not be too large and should not be too fine. The volume average diameter of oil globules (herein referred to simply as "average diameter of oil globules") should be in the range of between about 0.05 and about 30 mm, preferably between about 0.1 and about 10 mm.

As a method for measuring the average diameter of oil globules dispersed in an aqueous phase, a light transmission method, a photographic method and the like are known. In the method of the present invention, the reaction system is opaque, so that the light transmission method is not suitable for use in the present invention. Therefore, in the present invention, the photographic method is preferably employed for measuring the diameter of the oil globules dispersed in the aqueous phase. For example, 350 ml of water containing 0.2% by weight of a surfactant is placed in a transparent pressure vessel having a volume of 1000 ml, the internal pressure of which is kept at a level slightly lower than the internal pressure of the reactor (for example, a difference in pressure of 0.05 to 0.2 kg/cm² between the internal pressures), and about 10 ml of the reaction mixture containing oil globules is sampled from the reactor (in which the reaction system is in a circulated state) through a sampling nozzle and the sampled reaction mixture is placed in the transparent pressure vessel. The sampled reaction mixture is caused to be diluted with the water in the pressure vessel and the oil globules ascend to the surface of the water. When the oil globules are ascending toward the surface of the water, a photograph of the oil globules is taken. The photograph is magnified, for example, 2 to 100 times, and the diameters of about 150 to about 350 oil globules are measured by means of an ordinary scale, thereby determining an average value, which is taken as a volume average oil globule diameter. When the size of the oil globules is large and thus the globules are likely to aggregate with each other during the sampling before taking a photograph, the size of the equipment for the sampling is increased, thereby preventing the aggregation of the oil globules during the sampling.

Alternatively, measurement of the diameter of the oil globules can be conducted, without sampling the reaction mixture, by photographing the oil globules in the reactor through a peep window directly provided in the wall of the reactor.

The present inventors have studied as to which of the oil phase and the aqueous phase should be employed as a continuous phase. As a result, they have found that the activity lowering of the catalyst is markedly smaller when the aqueous phase is a continuous phase and the oil phase is a dispersed phase than in the opposite case. The reason would be that in the above-mentioned opposite case, a catalyst having a less amount of water adsorbed thereon is brought into contact with a large amount of cyclohexene and consequently a polymerization of cyclohexene occurs at the active sites of the catalyst, thereby poisoning the catalyst The reason for the lowering of the activity of the catalyst when the reaction system becomes emulsified would also be that the amount of an oil phase is large at emulsified portions of the reaction system and consequently a polymerization of cyclohexene poisons the active sites of the catalyst Therefore, in the present invention, it is requisite that the aqueous phase be a continuous phase. Too much of an increase of the number of dispersed oil globules as an oil phase is not appropriate in the present invention for the above-mentioned reason. Since cyclohexene from the dispersed oil phase becomes dissolved in the continuous aqueous phase before being adsorbed on the catalyst and without directly contacting the catalyst, the activity of the catalyst can be maintained at a high level for a prolonged period of time in the reaction system.

In the production of cyclohexanol by the hydration of cyclohexene, isomerization of cyclohexene occurs to form methylcyclopentenes, such as 1-methylcyclopentene, 3-methylcyclopentene and 4-methylcyclopentene. These methylcyclopentenes are hydrated to produce methylcyclopentanols as by-products. Further, the desired cyclohexanol may react with cyclohexene to produce dicyclohexyl ether as another by-product.

These by-products not only lower the yield of the desired cyclohexanol but also cause a large amount of energy to be wasted in the distillation of reaction products for obtaining purified cyclohexanol because the boiling points of cyclohexanol and by-products are very close to each other. The boiling points of cyclohexanol, 1-methylcyclopentanol and 3-methylcyclopentanol are 161° C., 154° C. and 163° C., respectively. Further, the recovery of cyclohexene from its isomers is difficult because of the closeness of their boiling points. The boiling points of cyclohexene, 1-methylcyclopentene and 3-methylcyclopentene are 83.0° C., 75.8° C. and 65.0° C., respectively.

The present inventors have studied the rate of formation of by-products. As a result, they have found that the rates of formation of methylcyclopentene and dicyclohexyl ether are in proportion to the zero-th power of the concentration of cyclohexene in the aqueous phase while the rate of conversion of cyclohexene to cyclohexanol is in proportion to the first power of the concentration of cyclohexene in the aqueous phase. They have also found that the rate of the conversion from methylcyclopentene to methylcyclopentanol is in proportion to the first power of the concentration of methylcyclopentene. When the mass transfer rate of cyclohexene in the interface between the oil phase and the aqueous phase is small, the main reaction to produce cyclohexanol is substantially inhibited while the reaction to produce methylcyclopentene and dicyclohexyl ether proceeds with certainty (although the by-production amount thereof is small), thereby causing the selectivity for cyclohexanol to be lowered. This effect is attributed to the dispersion of oil globules as an oil phase in the continuous aqueous phase including water, and is significant. Accordingly, the volume ratio of the oil phase to the aqueous phase in the reaction system is generally in the range of between about 0.001:1 and about 1.0:1, preferably between about 0.01:1 and about 0.8:1.

It is preferred that the cyclic alcohol concentration of cycloolefin feedstock be as low as possible, from the viewpoint of productivity per catalyst charge. On a commercial scale continuous process, an oil phase is withdrawn from a stationary zone and distilled in a distillation column having an outlet for withdrawing a cyclic alcohol at a bottom portion thereof and an outlet for withdrawing a cycloolefin at a top thereof. The cycloolefin recovered from this outlet is blended with a fresh cycloolefin, and recycled into the reactor. A large amount of energy is required to render the recovered cycloolefin substantially free of cyclic alcohol, so that the recovered and recycled cycloolefin generally contains a small amount (for example, about 1 to 2% by weight) of a cyclic alcohol.

As mentioned hereinbefore, the hydration reaction of the present invention is an equilibrium reaction. The lower the reaction temperature, the less the formation of by-products and the greater the equilibrium concentration of cyclic alcohol. However, the lower the reaction temperature, the smaller the reaction rate. Accordingly, it is not advantageous to perform a hydration reaction at an extremely low temperature in the presence of a large amount of catalyst so as to increase the concentration of cyclic alcohol.

The hydration reaction is generally performed at a temperature of between about 50° and 250° C., preferably between about 70° and 200° C. and most preferably between about 80° and 150° C.

The pressure in the reactor for use in the present invention is not particularly limited. However, it is generally preferred that a pressure be employed under which both of water and the charged cycloolefin are liquid.

Generally, the hydration reaction is conducted at a cyclic alcohol concentration of between about 30 and about 80%, based on the equilibrium concentration of cyclic alcohol. Therefore, the concentration of a cyclic alcohol in the hydration reactor is limited so that the oil phase as oil globules comprises a cycloolefin in an amount of between about 50 and about 100% by weight, preferably between about 60 and about 99.9% by weight, and a cyclic alcohol corresponding to the cycloolefin in an amount of between about 0 and about 50% by weight, preferably between about 0.1 and about 40% by weight, based on the weight of the oil phase.

Representative examples of cycloolefins to be hydrated in the present invention include cyclopentene, methylcyclopentene, cyclohexene, methylcyclohexene, cyclooctene and cyclododecene.

In the present invention, the hydration reaction may be carried out in the presence of an organic solvent, such as a halogenated hydrocarbon, an alcohol, an ether, a ketone and a phenol. Representative examples of halogenated hydrocarbons include methylene chloride, chloroform, tetrachloromethane, trichloroethane and tetrachloroethane, and bromides, iodides and fluorides corresponding to the above-mentioned chlorides. Representative examples of alcohols include alcohols having 1 to 10 carbon atoms, such as methanol, ethanol, isopropanol, n-propanol, isobutanol and n-butanol. Representative examples of ethers include monoether and higher ethers, such as dioxane, tetrahydrofuran, diethyl ether, diisopropyl ether, diamyl ether, dimethyl ethers of ethylene glycol or diethylene glycol, sulfones inclusive of dipropylsulfone and sulfolan, sulfoxides inclusive of dimethyl sulfoxide. Representative examples of ketones include acetone and methyl ethyl ketone. Representative examples of phenols include phenol and cresol. The above-mentioned organic solvents may be used in combination. The organic solvent can be contained in the oil phase, the aqueous phase or both, depending upon the properties of the solvent.

It is desired that the purity of a cycloolefin feedstock be high. However, it may contain impurities, such as aromatic hydrocarbons, such as benzene and toluene, naphthenes, such as cyclohexane and cyclopentane, and paraffins, such as pentane and hexane. The concentration of these impurities is desirably not greater than 30% by weight. Further, the cycloolefin may contain inorganic impurities, such as water, nitrogen, argon, carbon dioxide and carbon monoxide. Desirably, the hydration reaction is carried out in the absence of oxygen, because the oxygen is likely to cause an activity lowering of the catalyst.

The average particle diameter of the crystalline aluminosilicate to be suspended in the reaction system of the present invention is generally up to about 0.5 μm, preferably up to 0.1 μm, in terms of primary particle diameter. The smaller the particle diameter, the greater the catalytic effect of the catalyst. Generally, however, from a practical point of view, there is a preferable lower limit defined by crystallinity. Crystallinity means a symmetrical, regular, periodic arrangement of atoms, for which an X-ray diffraction is observed [see the description of "crystal" appearing in vol. 3, page 349 of *Kagaku Daijiten* (Encyclopedia of Chemistry) published by Kyoritsu Shuppan K.K., Japan, in 1963]. Accordingly, for occurrence of a certain period and for occurrence of an X-ray diffraction phenomenon, an upper-limit defined by a crystal structure is present with respect to the size of the crystalline aluminosilicate catalyst. In the present invention, the primary average diameter of the aluminosilicate catalyst is generally up to 0.5 μm as mentioned above, for which an X-ray diffraction is observed. The primary particle diameter is measured by means of a scanning electron micrograph (magnification: 20,000 to 100,000).

The crystaline aluminosilicate catalyst suitable for use in the present invention is comprised of silica and alumina as described, for example, in U.S. Pat. No. 4,588,846 the disclosure in the specification of which is incorporated herein by reference. The molar ratio of silica to alumina is not particularly limited. However, it is preferably at least 10:1, more preferably at least 20:1. When the molar ratio of silica to alumina is high, e.g., 10:1 or more, the acidity of acid points, which are active sites for the hydration of a cycloolefin, is increased while the amount of acid points is markedly decreased.

Depending upon the properties and reactivity of a cycloolefin as a feedstock, the aluminosilicate catalyst with a large diameter may not be satisfactory from the viewpoint of catalytic activity and selectivity for a cyclic alcohol in the hydration reaction, but if it is pulverized into a particle size as described above, the catalytic activity and selectivity of the aluminosilicate catalyst is remarkably improved due to an increase in active sites for the hydration reaction and other effects.

As long as the primary particle diameter of the aluminosilicate catalyst is within the above-mentioned range, secondary particles formed by agglomeration of the primary particles having a larger diameter can also be effectively used in the present invention. The secondary particle diameter of the aluminosilicate catalyst is preferably not larger than 50μm. When it is larger than 50 μm, the mass transfer of a cycloolefin and a cyclic alcohol is likely to be suppressed in the macropores of catalyst particles, thereby causing the rate of the hydration reaction to be low. Herein, when at least 50% by weight of all the particles of the aluminosilicate catalyst have a particular value of diameter of less, that value is described as the particle diameter of the catalyst.

Representative examples of crystalline aluminosilicate crystals suitable for use in the present invention include mordenite, boraxsite, clinobutyrorite, L-type zeolite, ZSM-type zeolite (for example, ZSM-5 and ZSM-11) manufactured and sold by Mobil Oil Corporation, U.S.A., chabazite and erionite. These aluminosilicates can be used in combination.

Further, the crystalline aluminosilicate catalyst may contain a metal element. Representative examples of crystalline aluminosilicate catalysts containing a metal element include aluminosilicates containing a thorium element (see Japanese Patent Application Laid-Open Specification No. 60-248632/1985), aluminosilicates containing at least one element selected from the group consisting of copper and silver (see Japanese Patent Application Laid-Open Specification No. 60-248633/1985), aluminosilicates containing at least one element selected from the group consisting of chromium, molybdenum and tungsten (see Japanese Patent Application Laid-Open Specification No. 60-248634/1985), and aluminosilicates containing at least one element selected from the group consisting of titanium, zirconium and hafnium (see Japanese Patent Application Laid-Open Specification No. 60-248635/1985).

The crystalline aluminosilicate catalyst can be synthesized by various methods, including those in which the synthesis is performed in the presence of urea compounds (see Japanese Patent Application Laid-Open Specification Nos. 61-68319/1986 and 61-180735/1986) and methods in which the synthesis is performed in the presence of cyanoalkenes (see Japanese Patent Application Laid-Open Specification Nos. 62-017/1987, 63-154633/1988, 63-315512/1988 and 61-1141/1986). The methods for synthesizing the suitable aluminosilicate catalysts also include those in which only inorganic materials are employed (see Japanese Patent Application Laid-Open Specification Nos. 1-180835/1989 and 1-190644/1989) and methods in which the synthesis is performed in the presence of an amine (see Japanese Patent Application Laid-Open Specification No. 1-192717/1989). When the amount of the aluminosilicate catalyst suspended in the aqueous phase of the reaction system according to the present invention is too small, the rate of the hydration reaction is too low, thereby causing an extremely large reactor to be inevitably required to a disadvantage in commercial production. On the other hand, when the amount is too large, the viscosity of the aqueous phase is so high as to cause poor fluidity, which retards the diffusion of cycloolefin into the aqueous phase, thereby lowering the reaction rate of hydration. Accordingly, the weight ratio of the crystalline aluminosilicate catalyst to the water present in the reaction system is preferably between about 0.01:1 and about 2.0:1, more preferably between about 0.1:1 and about 1.0:1.

As mentioned above, the hydration reaction is generally performed at a temperature of between about 50° and 250° C., preferably between about 70° and 200° C. and most preferably between about 80° and 150° C. The pressure in the reactor for use in the present invention is not particularly limited. However it is generally preferred that a pressure be employed at which the water and cycloolefin are liquid.

In the present invention, it is requisite that the oil phase be dispersed in the continuous aqueous phase as globules having an average diameter of between about 0.05 and about 30 mm. This dispersion can be effectively performed by injecting the oil phase into the continuous aqueous phase through a disperser head having a plurality of orifices and/or conducting a mechanical dispersion while applying a shearing force to the reaction system by means of an agitator or the like. For attaining the above-mentioned dispersion, it is required to apply an external force to the oil phase for a period of time sufficient to cause the oil phase to be divided, the external force being sufficient to overcome the surface tension, interfacial pressure and viscous stress of the oil and aqueous phases. A satisfactory external force can be provided by employing a disperser head having orifices with a decreased diameter and increasing the injection speed of the oil phase. The satisfactory external force can also be provided by increasing the shearing force applied by an agitator, in particular by increasing the electric power used for agitation (hereinafter frequently referred to as "agitating power"), when an agitator is employed for attaining the desired dispersion.

With reference to FIGS. 1 to 9, several modes of the method of the present invention for performing the hydration of a cycloolefin are described hereinbelow, which, however, should not be construed as limiting the present invention.

In FIG. 1, there is shown a diagrammatic view illustrating one mode (first mode) of the method of the present invention, in which a reactor is shown in cross-section to show the interior thereof. Reactor 4 has at a lower portion thereof disperser head 6, connected to feed pipe 3, having a plurality of orifices. Reactor 4 is equipped with a thermometer protecting sheath (not shown) having a thermometer therein (not shown) for measuring the temperature of a reaction system and also with a pressure gauge (not shown) for measuring the pressure in reactor 4. Reactor 4 has at an upper portion thereof an oil phase outlet connected to pipe 5 for withdrawing the oil phase comprised of produced cyclohexanol and unreacted cyclohexene. The above-mentioned feed pipe 3 is connected to pipe 1 for feeding cyclohexene and pipe 2 for feeding water. Feed pipe 3 is also connected to a circulation conduit branched off from oil phase withdrawing pipe 5 so that the withdrawn oil phase is partly recycled to reactor 4 by means of pump 8 and injected from the orifices of disperser head 6. An electric heater (not shown) is attached to the outer surface of reactor 4, and all of the above-mentioned pipes have flow meters (not shown) for measuring the flow rate of fluid passed therethrough. Disposed in the side wall of cylindrical reactor 4 is a glass peep window not shown for observing the separation condition of an oil phase layer from a continuous aqueous phase including water and oil globules suspended therein and for determining the position of the interface between the oil phase layer and the continuous aqueous phase.

That is, according to this mode (first mode) of the method of the present invention, the reaction is conducted in a reactor having at a lower portion thereof at least one disperser head, connected to a feed pipe, having a plurality of orifices, and further having at an upper portion thereof an oil phase outlet connected to means for withdrawing an oil phase, obtained by the reaction, comprising produced cyclic alcohol and unreacted cycloolefin. An oil phase is fed through the feed pipe and injected from the orifices into the reaction system, thereby dispersing and circulating the oil phase in the continuous aqueous phase as oil globules having an average diameter of between about 0.05 and about 30 mm. A continuous oil phase layer, formed in an upper portion of the reactor due to unification of oil globules obtained by the reaction, is withdrawn through the outlet and the withdrawing means and partly recycled to the reactor through a circulation conduit branched off from the oil phase withdrawing means and connected to the feed pipe, so that the recycled oil phase is injected from the orifices of the disperser head.

The shape of reactor 4 is not particularly limited, and it may be of a vertical type or a horizontal type and may be in the form of a rectangular parallelopiped or a cylinder However, it is generally desired to avoid accumulation of slurry and stagnation of liquid, and from this viewpoint, the most preferred shape of the reactor is a vertical cylinder.

When a cycloolefin is passed only once through the reactor without recycling, the volume ratio of the oil globules phase to the aqueous phase is not sufficient so that the overall hydration reaction rate is likely to be limited by mass transfer. This can be avoided by recycling to the reactor a continuous oil phase layer, formed in an upper portion of the reactor by unification of oil globules obtained by the reaction and injecting the recycled oil phase from the orifices of the disperser head so that the volume ratio of the oil phase to the aqueous phase is increased. The greater the amount of the recycled oil phase, the greater the volume ratio increase. However, in the present invention, the continuous phase should be comprised of the aqueous phase, as mentioned above. Therefore, generally, the weight ratio of the recycled oil phase to cycloolefin feed is between about 1:1 and about 150:1.

The disperser head for injecting the oil phase into the reaction system has a plurality of orifices preferably with an inner diameter of between about 0.3 and about 10.0 mm. Such a disperser head can be effectively used alone when the cycloolefin is of a type such that unification of oil globules rapidly occurs. However, when the reaction system is likely to suffer from emulsification, pipes each having a length of between about 10 and about 200 mm and an inner diameter of 2 to 5 times the diameter of the orifice for avoiding formation of too fine oil globules are preferably attached to the disperser head so as to enclose the respective orifices.

The number of disperser heads is increased depending upon the size of the reactor to render the dispersion of the oil phase uniform.

According to another mode (second mode) of the present invention, the hydration reaction is conducted in a reactor having an agitator with a plurality of agitating blades. When the agitator is operated, the entire reaction system is agitated to produce a shearing force, thereby dispersing the oil phase in the continuous aqueous phase while preventing the catalyst suspended in the continuous aqueous phase from settling, and dividing aggregated oil globules, formed in the reaction system at places distant from the agitating blades, into re-dispersed oil globules.

Figure 2:
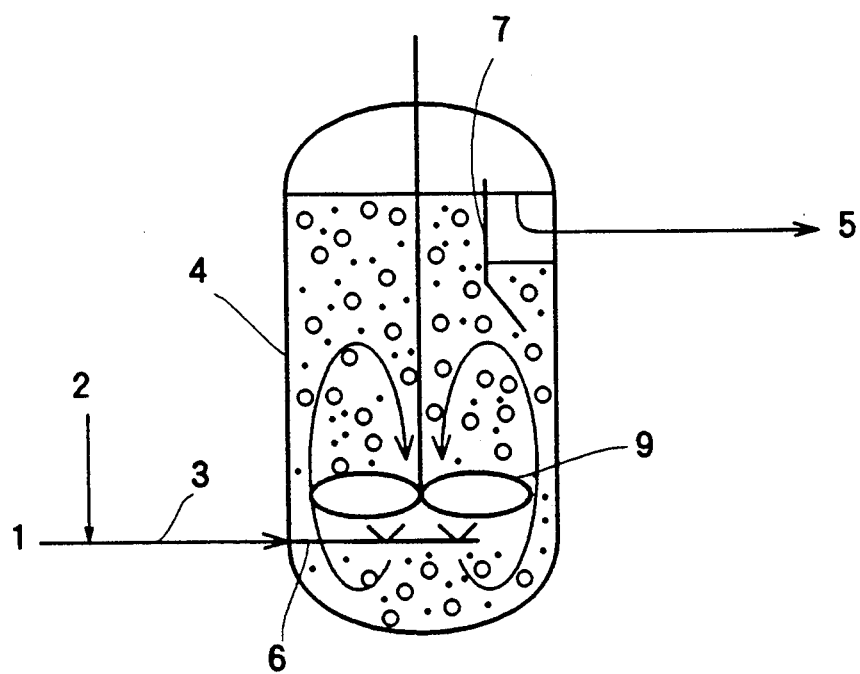
FIG. 2 is a diagrammatic view illustrating another mode of the method of the present invention, in which a reactor further having an agitator is shown in cross-section to show the interior thereof.

FIG. 2 shows a diagrammatic view illustrating the second mode of the method of the present invention utilizing an agitator. As in reactor 4 for use in the first mode of the method of the present invention, reactor 4 includes disperser head 6, connected to feed pipe 3, having a plurality of orifices and an oil phase outlet connected to pipe 5 for withdrawing an oil phase, obtained by the hydration reaction, comprised of produced cyclohexanol and unreacted cyclohexene, the feed pipe 3 being connected to pipe 1 for feeding cyclohexene and pipe 2 for feeding water As different from reactor 4 for use in the first mode of the method of the present invention, reactor 4 is provided with an agitator with a plurality of agitating blades 9 for agitating the entire reaction system to produce a shearing force, thereby dispersing the oil phase in the continuous aqueous phase while preventing the catalyst suspended in the continuous aqueous phase from settling, and dividing aggregated oil globules, formed in the reaction system at places distant from the agitating blades, into re-dispersed oil globules, and is also provided with weir 7 around the oil phase outlet for providing a stationary zone to thereby facilitate separation of a reaction mixture obtained by the reaction into an upper oil phase layer comprising a produced cyclic alcohol and a lower aqueous phase layer having the catalyst suspended therein.

Agitating blades 9 of the agitator may preferably be of a turbine blade type, a propeller type and a paddle type. Particularly preferred is a propeller type because it generates vertically circulating flow with small power so that the formation of too fine oil globules can be prevented.

The axis of the agitator is not necessarily disposed in the center of reactor 4. Either one agitator or a plurality of agitators may be employed in the hydration method of the present invention.

The agitator may have either a single set of agitating blades 9 arranged in a common plane (hereinafter referred to simply as "blade set") or a plurality of blade sets arranged in tiers, which may be structurally identical or different.

In the method of the present invention, it is preferred that the reaction system be agitated so as to produce downward flow components, so that the oil phase including a cycloolefin can be circulated in the form of a mixture with the aqueous phase. Illustratively stated, for mixing the oil phase, which has a specific gravity smaller than that of the aqueous phase, with the aqueous phase, it is preferred that the agitated reaction system contain downward flow components serving to forcibly move downward oil globules which are ascending due to the small specific gravity. The downward flow components may be produced either in the center portion of the reactor, as shown in FIG. 2, or in a portion laterally apart from the center portion.

For dispersing the oil phase into the aqueous phase, disperser head 6 having a plurality of orifices employed in the first mode of the method of the present invention can be effectively used in the second mode of the method of the present invention. However, it is generally preferred that the dispersion be performed in a reactor having a structure such that the agitator has several small turbine blades and has, fixed thereto, a feed pipe for the oil phase to be fed above or below the turbine blades. In this mode of dispersion, oil globules having an appropriate diameter are produced, which are entrained by the agitation flow so that a sufficient time is ensured for the fed oil phase to remain in the reaction system for hydration reaction, without formation of too large globules followed by immediate pass through the reaction system. Further, this mode of dispersion is advantageous because the diameter of the feed pipe can be large so that scaling and choking by the catalyst can be avoided.

Figure 3:
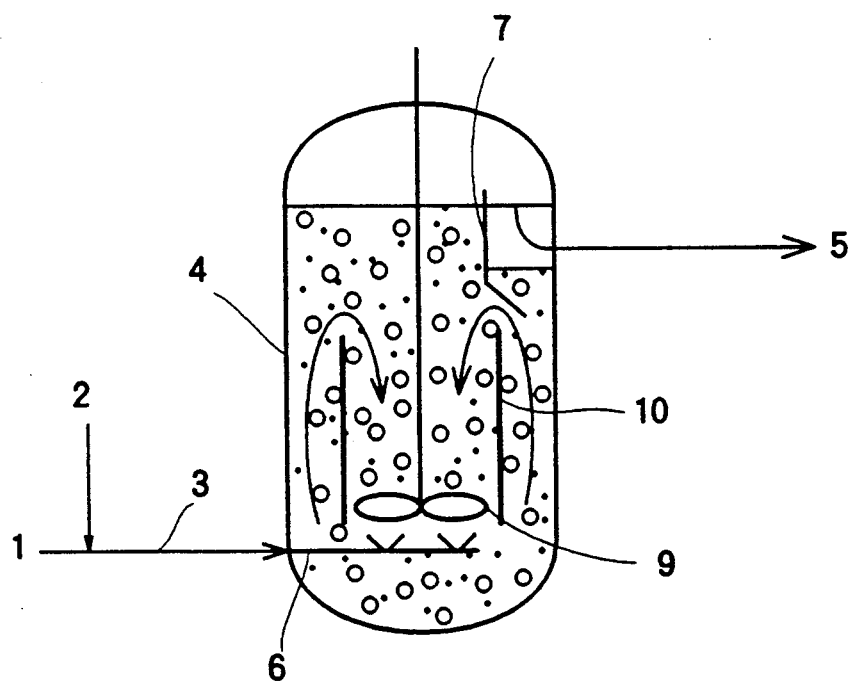
FIG. 3 is a diagrammatic view illustrating still another mode of the method of the present invention utilizing a reactor further having a hollow cylinder disposed therein as a draft tube.

Referring to FIG. 3, in order to enhance the effect of the agitation, the reactor of FIG. 2 is further provided with hollow cylinder 10. Illustratively stated, reactor 4 has, disposed therein, hollow cylinder 10 having an inner and an outer wall and a top and a bottom open end to enclose the agitator, providing a first spacing between the agitator and the inner wall of the cylinder within the reaction system in the reactor and providing a second spacing between the outer wall of the cylinder and the inner wall of the reactor within the reaction system in the reactor, the cylinder having a horizontal cross-section area sufficient to cause the reaction system to be circulated through the first and second spacings within the reactor, so that the cylinder 10 functions as a draft tube. It is generally preferred that agitating blades 9 be completely enclosed in hollow cylinder 10. However, substantially the same effect can be obtained even if they partly protrude from hollow cylinder 10. Hollow cylinder 10 is generally fixed to the inner wall of reactor 4. The fixing method of hollow cylinder 10 to the inner wall of reactor 4 is not particularly limited as long as the fixing withstands stress due to the circulation of the reaction system and as the means for the fixing does not block the circulation of the reaction system. The means for the fixing may be a metal plate.

By virtue of hollow cylinder 10, downward flow is promoted, and the oil phase and the aqueous phase can be effectively agitated and mixed with small agitating power so that a satisfactory reaction rate is ensured for the hydration of a cycloolefin. Further, too strong agitation can be avoided so that too fine oil globules are not formed to thereby facilitate the separation of the oil phase from the aqueous phase in a stationary zone after the hydration reaction. Still further, the effective mixing with less agitation by virtue of hollow cylinder 10 has resolved various drawbacks having been caused by too strong agitation, such as catalyst loss and filter choking at the time of catalyst regeneration which are attributed to decomposition of the catalyst caused by too strong agitation.

By the use of a hollow cylinder 10, the agitating power can be reduced to 1/5-1/10 as compared to that required for the reactor without a hollow cylinder, while achieving the same yield.

Reactor 4 preferably has at least one vertically extending baffle plate substantially centripetally projecting from the inner side wall of the reactor and terminating at a position near the side wall, with a spacing remaining above and below the baffle plate within the reaction system. The longer the baffle plate, the more effectively the reaction system is vertically circulated. The baffle plate is generally fixed to the inner wall of the reactor. The fixing method is not particularly limited as long as the baffle plate is perpendicular to the wall of the reactor.

The number of baffle plates is increased as the size of an agitation zone defined by the agitator is increased.

The baffle plate is preferably used in combination with hollow cylinder 10. This advantageously promotes the downward flow of the reaction system. The baffle plate alone can be used without combining it with hollow cylinder 10 shown in FIG. 3 and can exert its inherent effect.

The separation of the oil phase from the aqueous phase to thereby take out only the oil phase including a produced cyclic alcohol, can be attained by disposing weir 7 around an outlet for a reaction product as an oil phase (which is connected to withdrawing pipe 5) so that a stationary zone to facilitate phase separation is provided, as shown in FIGS. 2 and 3. That is, when the reaction mixture is allowed to stand still in the stationary zone, the oil globules are caused to ascend, to thereby form a continuous oil phase as an upper layer and a continuous aqueous phase as a lower layer in the stationary zone. Then, the continuous oil phase is withdrawn through outlet pipe 5 and a cyclic alcohol is then isolated from the oil phase. On the other hand, the continuous aqueous phase separated from the oil phase descends due to its specific gravity which is higher than the reaction mixture, so that the separated aqueous phase is replaced with the reaction mixture. The reaction mixture is then separated into the oil phase and the aqueous phase as mentioned above Referring to FIG. 4, as an alternative method for separating the oil phase from the aqueous phase, there is a method in which a reaction mixture, obtained by the hydration reaction, comprising an oil phase and an aqueous phase is introduced through conduit 12 into oil phase-aqueous phase separator 11 disposed outside reactor 4 to effect separation between the oil phase and the aqueous phase. The oil phase is separated as an upper layer including a produced cyclic alcohol and the aqueous phase is separated as a lower layer including water and the aluminosilicate catalyst suspended therein. The lower layer is recycled through conduit 13 to reactor 4. The upper layer is partly withdrawn through pipe 5 and partly recycled to reactor 4 by means of pump 8, as in the first mode of the method of the present invention. The transfer of the reaction mixture from reactor 4 to oil phase-aqueous phase separator 11 through conduit 12 and the transfer of the aqueous phase from oil phase-aqueous phase separator 11 to reactor 4 through conduit 13 can be performed by gravity or a pump.

The formation of oil globules having an appropriate diameter is easier in reactor 4 devoid of a stationary zone than in a reactor with a stationary zone, which oil globules ensure efficient separation of the oil phase from the aqueous phase in oil phase-aqueous phase separator 11.

Figure 5:
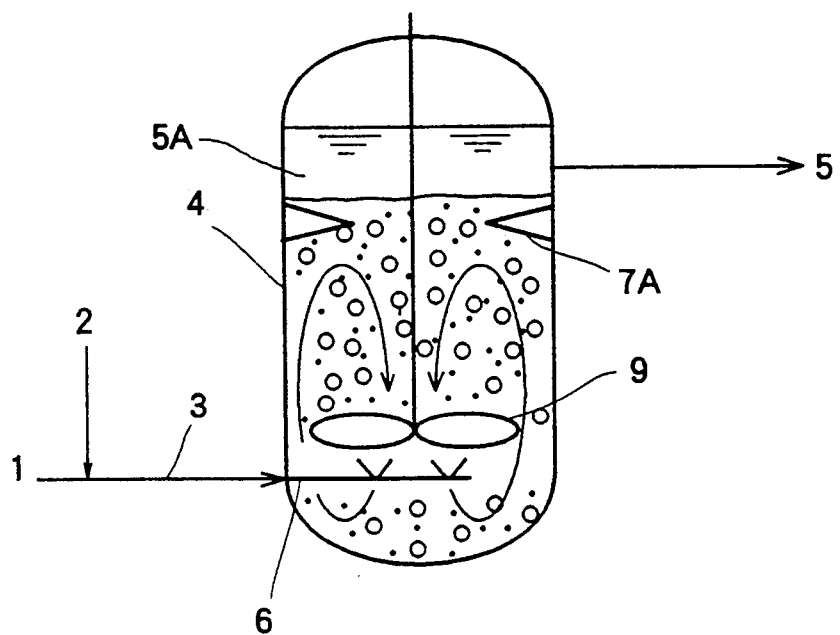
FIG. 5 is a diagrammatic view illustrating still a further mode of the method of the present invention utilizing a reactor partitioned by means of a partition member.

In place of the above-mentioned separation using oil phase-aqueous phase separator 11, the separation of a large volume of reaction mixture can be achieved by a method using a reactor provided with a partition member. As shown in FIG. 5, reactor 4 is partitioned by means of partition member 7 to provide an agitation zone as a lower zone and stationary zone 5A as an upper zone. The reaction system is agitated in the agitation zone to produce a shearing force so that the oil phase is dispersed in the continuous aqueous phase as the oil globules, while partition member 7 allows the oil globules to flow from the agitation zone to stationary zone 5A so that unification of the oil globules occurs in stationary zone 5A to form a continuous oil phase layer therein.

Specific examples of partition members include a perforated disk with its periphery directly connected to the inner side wall of the reactor; a non-perforated disk with its periphery connected to the inner side wall of the reactor through a support, with a gap provided between the periphery and the inner side wall; a grid deck with its periphery directly connected to the inner side wall of the reactor; a flat doughnut plate with its periphery directly connected to the inner side wall of the reactor; a doughnut plate having a hollow truncated cone form with its open bottom directed upwardly, the periphery of the open bottom being directly connected to the inner side wall of the reactor; a doughnut plate having a hollow truncated cone form with its open top directed upwardly, the periphery of the open bottom being connected to the inner side wall of the reactor through a support, with a gap provided between the periphery and the inner side wall of the reactor; and a doughnut plate composed of a pair of hollow truncated cones with their respective open tops connected to each other and with their open bottoms respectively directed upwardly and downwardly, the periphery of the open bottom of each cone being connected to the inner side wall of the reactor.

FIG. 6 (a) shows a diagrammatic perspective view illustrating doughnut plate 7A-1 disposed in reactor 4 to provide stationary zone 5A-1 as an upper zone and an agitation zone as a lower zone. The doughnut plate is composed of a pair of hollow truncated cones with their respective open tops connected to each other and with their open bottoms respectively directed upwardly and downwardly, the periphery of the open bottom of each cone being connected to the inner side wall of the reactor FIG. 6 (b) shows a diagrammatic perspective view illustrating a form of perforated disk 7A-2 disposed in reactor 4 to provide stationary zone 5A-2 as an upper zone and an agitation zone as a lower zone.

In addition, baffle means having a respective configuration shown in FIGS. 9(b) through 9(e) as described hereinafter in connection with the forth mode of the method of the present invention can also be used as the above-mentioned partition member.

According to a further mode (third mode) of the method of the present invention, the hydration reaction of a cycloolefin is conducted using a plurality of reactors connected in series and comprising a first reactor and at least one additional reactor. A reaction mixture, which is obtained in a reactor preceding the additional reactor and comprises a produced cyclic alcohol and an unreacted cycloolefin, is introduced to the additional reactor to thereby hydrate the unreacted cycloolefin.

Figure 7:
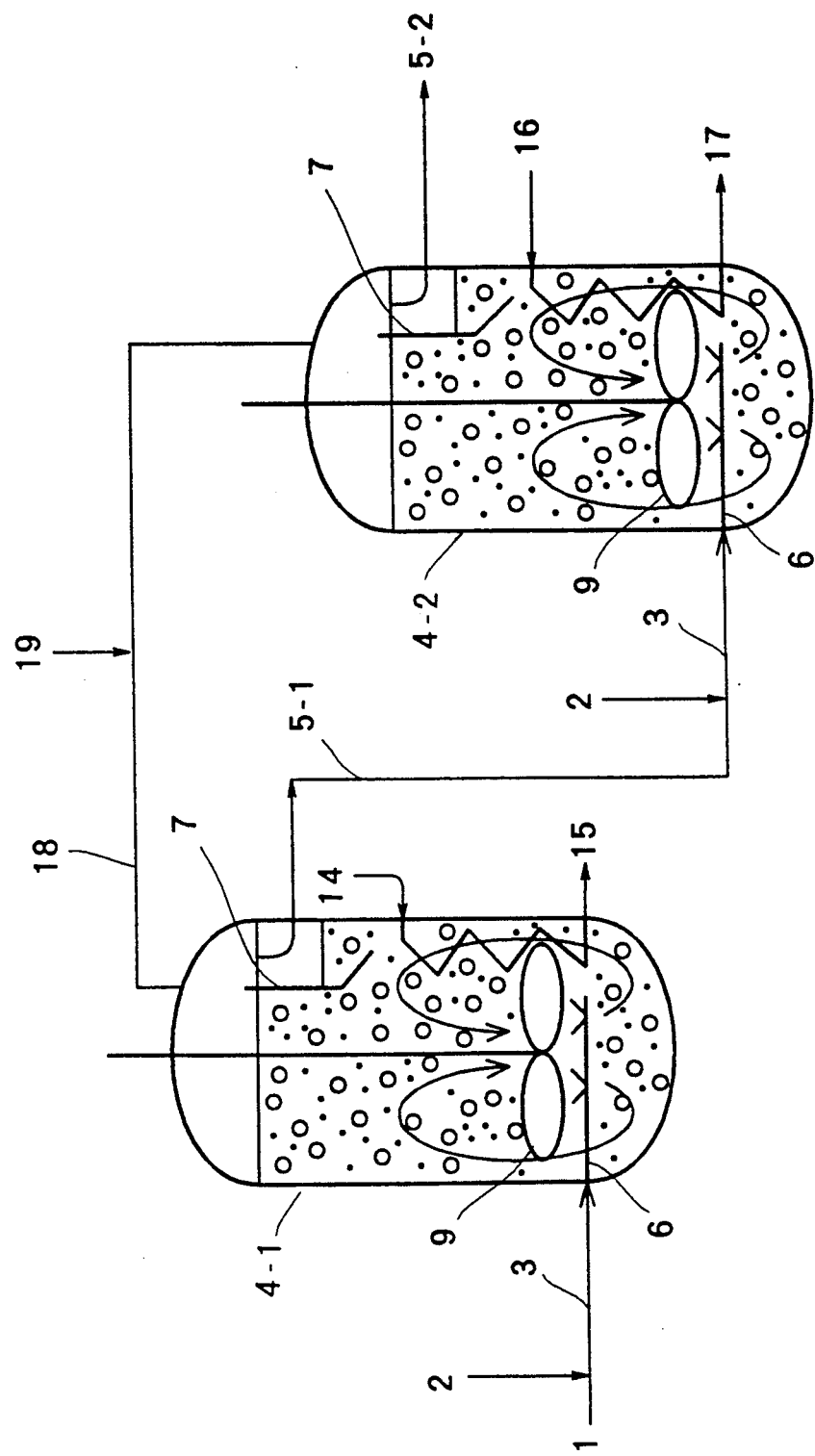
FIG. 7 is a diagrammatic view illustrating still a further mode of the method of the present invention utilizing two reactors connected in series.

FIG. 7 shows a diagrammatic view illustrating the third mode of the method of the present invention utilizing two reactors connected in series. First reactor 4-1 is equipped with an agitator having blades 9, feed pipe 3 for feeding an oil phase including a cycloolefin which is fed through pipe 1 and for introducing water which is fed through pipe 2, and disperser head 6 connected to feed pipe 3. The first reactor is further equipped with weir 7 for providing a stationary zone. The first reactor is still further equipped with a steam heater having steam inlet 14 and steam outlet 15. The oil phase separated in the stationary zone of the first reactor is transferred to additional reactor 4-2 through withdrawing pipe 5-1 and feed pipe 3 provided at a lower portion of additional reactor 4-2. Additional reactor 4-2 has substantially the same structure as that of first reactor 4-1, except that a cooler having cooling water inlet 16 and cooling water outlet 17 is disposed in place of the steam heater. The oil phase introduced into additional 4-2 reactor undergoes the hydration reaction therein, and withdrawn through pipe 5-2. The withdrawn oil phase may either entirely be subjected to distillation for isolation of produced cyclic alcohol, or partly recycled to the first reactor. First reactor 4-1 and additional reactor 4-2 are communicated with each other through pipe 18 for equating the pressure in first reactor 4-1 with the pressure in additional reactor 4-2. The pressures can be equated by an inert gas fed through pipe 19 connected to pipe 18.

Figure 4:
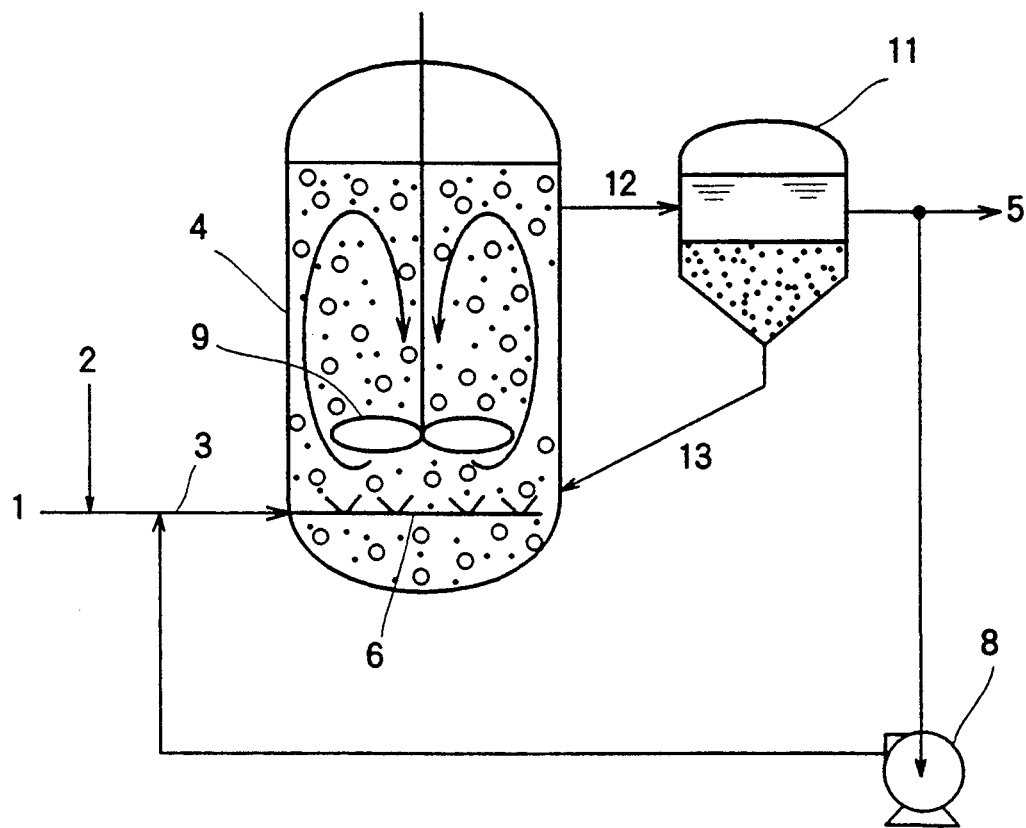
FIG. 4 is a diagrammatic view illustrating a further mode of the method of the present invention utilizing a reactor connected to an oil phase-aqueous phase separator disposed outside thereof.

In the third mode of the method of the present invention, an example of which is shown in FIG. 7, circulation conduits may be branched off from respective oil phase withdrawing pipes 5-1 and 5-2 of reactors 4-1 and 4-2 in substantially the same manner as in FIGS. 1 and 4 so that respective withdrawn oil phases are partly recycled to the reactors by means of pumps and injected from the orifices of the disperser heads disposed in respective lower portions of the reactors, in a manner similar to those shown in FIGS. 1 and 4.

The lower the hydration reaction temperature, the greater the equilibrium conversion of a cycloolefin to a cyclic alcohol. On the other hand, a decrease in hydration reaction temperature retards the hydration reaction. Accordingly, for increasing the one-pass reaction yield of a cyclic alcohol, the cycloolefin must be contacted with a large amount of catalyst at a low temperature for a prolonged period of time in a large reactor. These are unfavorable from the viewpoint of productivity.

The present inventors have found that this problem can successfully be coped with by the following method. That is, the problem can be coped with by using a plurality of reactors connected in series in which the temperatures of the plurality of reactors are controlled so as to be successively lowered in accordance with a direction of flow of the reaction system through the reactor.

Further, in the third mode of the method of the present invention, the reaction system assumes a piston flow through a plurality of reactors connected in series, so that the concentration of produced cyclic alcohol in the oil phase approaches an equilibrium concentration which is generally in the range of between about 10 and about 40% by weight, thereby improving the reaction yield by one pass through the reactor.

The effect of the above-mentioned third mode of the method of the present invention using a plurality of reactors connected in series can also be achieved by using a reactor which is partitioned by means of baffle means into a plurality of chambers arranged in tiers so that each chamber contains at least one set of the blade sets. An example of such a reactor is shown in FIG. 8.

Figure 8:
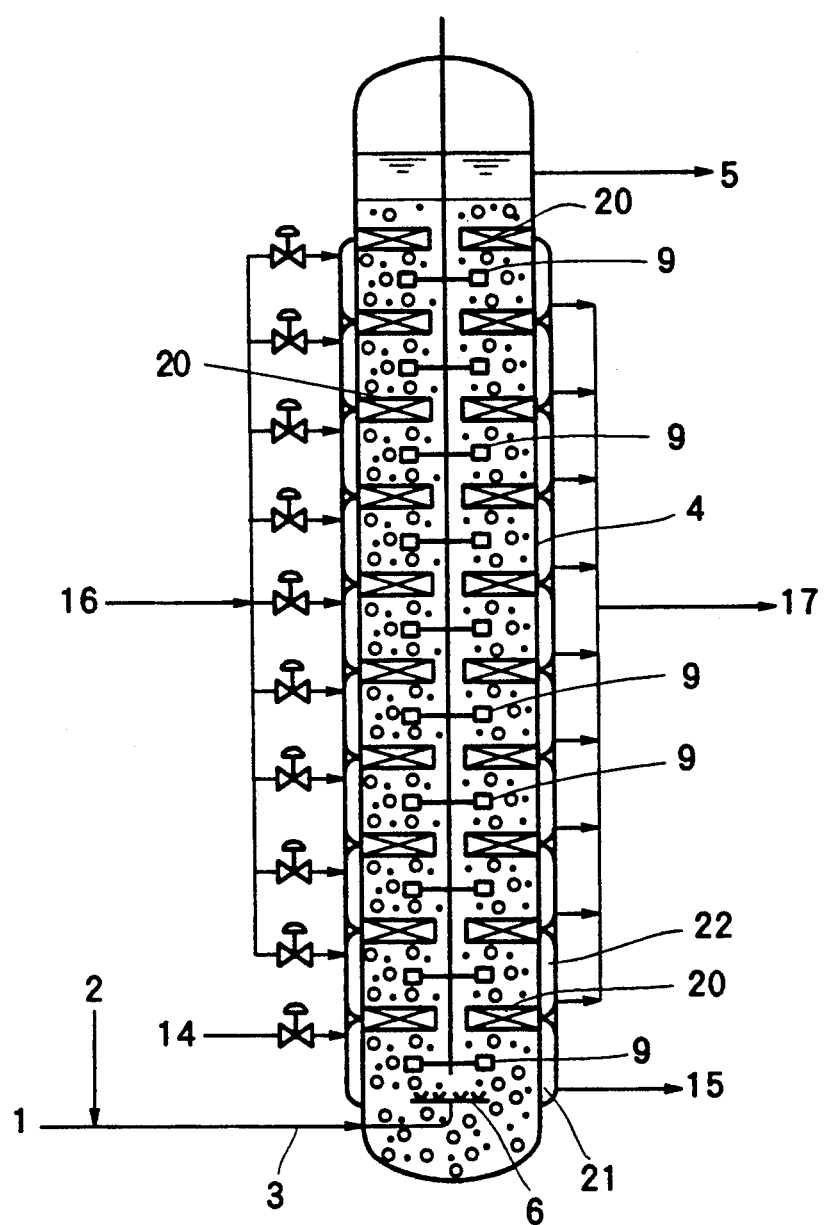
FIG. 8 is a diagrammatic view illustrating still a further mode of the method of the present invention utilizing a reactor having an agitator with a plurality of blade sets arranged in tiers, the reactor being partitioned by means of baffle means into a plurality of chambers each containing one of the blade sets.

Accordingly, in still a further mode (fourth mode) of the method of the present invention, as shown in FIG. 8, the reaction is conducted in reactor 4 having an agitator with a plurality of agitating blades 9 for producing the shearing force, the plurality of agitating blades 9 including a plurality of blade sets arranged in tiers, wherein reactor 4 is partitioned by means of baffle means 20 into a plurality of chambers arranged in tiers so that each chamber contains at least one set of the blade sets, providing independent agitation zones for the reaction system.

In the fourth mode of the method of the present invention, the entire reaction system in each chamber is agitated by means of the agitator provided therein to produce a shearing force, thereby dispersing the oil phase in the continuous aqueous phase while preventing the catalyst suspended in the continuous aqueous phase from settling and dividing aggregated oil globules, formed in the reaction system in each chamber at places distant from the agitating blades, into re-dispersed oil globules.

Baffle means 20 allows the reaction system to flow from a first chamber of two mutually adjacent chambers partitioned by the baffle means to a second chamber of the adjacent chambers in accordance with a predetermined direction of flow of the reaction system. Baffle means 20 prevents flow of the reaction system in a counter direction to the predetermined direction, so that the reaction system in the second chamber is prevented from being back-mixed with the reaction system in the first chamber. Thus, each of the chambers partitioned by baffle means 20 can function as a separate reactor having an agitator.

As shown in FIG. 8, the uppermost baffle means may provide an agitation zone as a lower zone and a stationary zone as an upper zone, which are, respectively, positioned below and above the uppermost baffle means, and wherein the reaction system is agitated in the agitation zone to produce the shearing force so that the oil phase is dispersed in the continuous aqueous phase as the oil globules, while the baffle means allows the oil globules to flow from the agitation zone to the stationary zone so that unification of the oil globules occurs in the stationary zone to form a continuous oil phase layer therein.

Baffle means 20 is not particularly limited and can be, for example, a perforated plate, a net-like structure, a doughnut type, a semilunar plate, a grid deck, a cone-shaped angle deck, and a plate which is disposed in reactor 4 so that a gap is left between the periphery of the plate and the inner wall surface of the reactor. Various types of baffle means may be used individually or in combination.

Figure 9C:
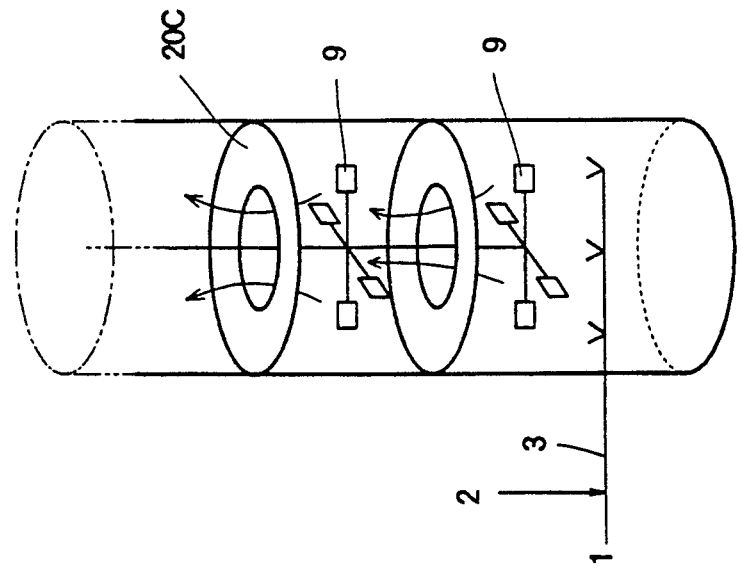
FIGS. 9 (a) through 9 (f) are diagrammatic views showing various types of baffle means, such as a perforated plate [FIG. 9(a)], a disk type plate [FIG. 9(b)], a doughnut type plate [FIG. 9(c)], another doughnut type plate [FIG. 9(d)], still another doughnut type plate [FIG. 9(e)] and a further doughnut type plate [FIG. 9(f)].
Figure 9B:
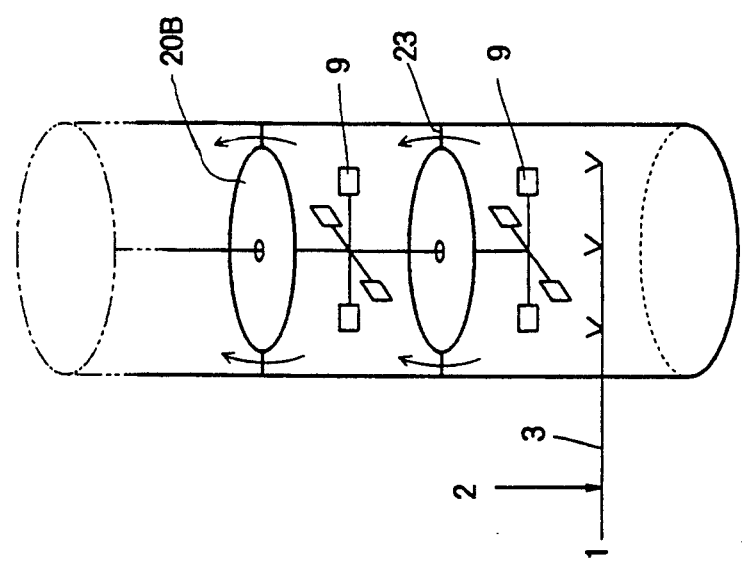
Figure 9A:
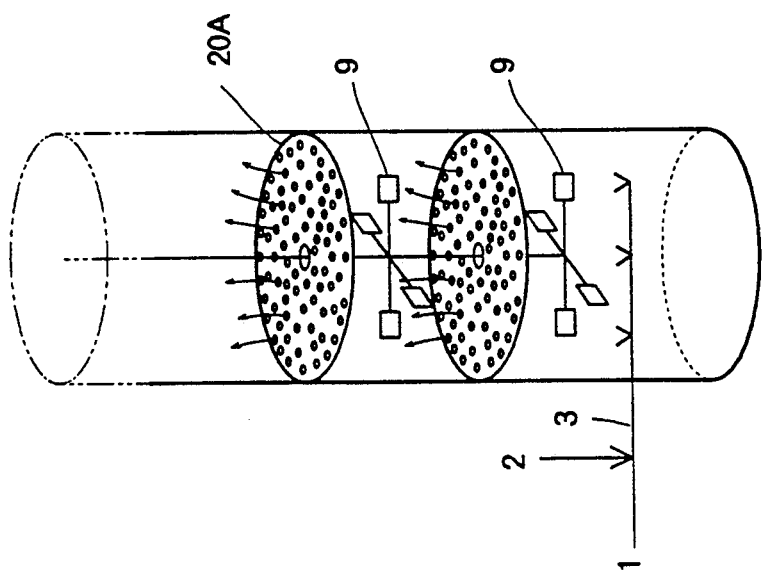

In FIGS. 9(a), 9(b), 9(c), 9(d), 9(e) and 9(f), six types of baffle means are shown. FIG. 9(a) shows an example of baffle means of perforated plate 20A. FIG. 9(b) shows another example of baffle means of plate 20B which is disposed in reactor 4 so that a gap is left between the periphery thereof and the inner wall surface of reactor 4, and which can be fixed to the inner wall surface of reactor 4 by means of support 23. FIG. 9(c) shows still another example of baffle means of flat doughnut type plate 20C with its periphery directly connected to the inner side wall of the reactor. FIG. 9(d) shows a further example of baffle means of doughnut plate 20C-1 having a hollow truncated cone form with its open bottom directed upwardly, the periphery of the open bottom being directly connected to the inner side wall of the reactor. FIG. 9(e) shows still a further example of baffle means of doughnut plate 20C-2 having a hollow truncated cone form with its open top directed upwardly, the periphery of the open bottom being connected to the inner side wall of the reactor through a support, with a gap provided between the periphery and the inner side wall of the reactor. FIG. 9(f) shows still a further example of baffle means of doughnut plate 20C-3 composed of a pair of hollow truncated cones with their respective open tops connected to each other and with their open bottoms respectively directed upwardly and downwardly, the periphery of the open bottom of each cone being connected to the inner side wall of the reactor.

When baffle means 20 is used, the reaction system is flowed through baffle means 20 in a direction indicated by arrow in the respective Figure.

The ratio of the height of a chamber (i.e., agitation zone) formed between two adjacent baffle means 20, 20 to the diameter of the reactor is preferably 0.2 to 2. The type of agitating blades 9 may or may not be different between the agitation zones. The position of a blade set in each agitation zone is preferably in the middle of the height of the agitation zone, but the position is not particularly restricted as long as a satisfactory agitation can be attained.

Referring back to FIG. 8, reactor 4 is further provided with cooling jacket 22 having cooling water inlet 16 and cooling water outlet 17 and also with steam jacket 21 for controlling the temperature of the reaction system in reactor 4.

In chambers positioned near feed pipe 3, the concentration of produced cyclic alcohol in the oil phase is still low and below an equilibrium concentration. Accordingly, in such chambers, it is preferred from the viewpoint of productivity per unit of catalyst charge that the temperature be increased so as to increase the reaction rate from a cycloolefin to a cyclic alcohol. On the other hand, in chambers positioned near withdrawing pipe 5, the concentration of produced cyclic alcohol in the oil phase is high, approaching an equilibrium concentration, so that the temperature is desirably controlled to be relatively low to thereby ensure a high equilibrium concentration even if the reaction rate is lowered.

Therefore, in a reactor partitioned by means of baffle means into a plurality of chambers, it is preferred that the temperatures of the plurality of chambers are controlled so as to be successively lowered in accordance with a direction of flow of the reaction system through the chambers.

The hydration reaction of a cycloolefin is an exothermic reaction. Hence, if an adiabatic reaction is performed in a reactor partitioned by means of baffle means into a plurality of chambers, the temperatures of chambers are successively increased in the direction of flow of the reaction system through the chambers, thereby lowering the one-pass reaction yield of a cyclic alcohol. Accordingly, cooling of chambers for coping with the temperature elevation due to the exothermic reaction is generally performed, in addition to heating of chambers for initiating the hydration reaction. In particular, it is preferred that in chambers positioned near feed pipe 3 the chamber be set at 110°–170° C. and in chambers provided near withdrawing pipe 5 the temperature be set at 1°–30° C. below the temperature of chambers positioned near feed pipe 3, while in chambers positioned therebetween the temperatures be successively lowered in accordance with a direction of flow of the reaction system.

The heating and cooling of chambers may be performed by circulating steam or cooling water through a coiled pipe disposed in the reactor or a jacket attached to the reactor. Preferably, the amount of passed steam or cooling water is independently controlled for each of the chambers.

For obtaining a reaction product, the uppermost chamber of the chambers may be provided with an outlet for a reaction product as an oil phase, and also with a weir around the outlet for providing a stationary zone to thereby facilitate separation of a reaction mixture obtained by the reaction into an upper oil phase layer comprising a produced cyclic alcohol and a lower aqueous phase layer comprising the water and the catalyst suspended therein.

Alternatively, as shown in FIG. 4, a reaction mixture obtained by reactor 4, as such, may be introduced into an oil phase-aqueous phase separator disposed outside of the reactor to thereby separate the oil phase as an upper layer comprising a produced cyclic alcohol from the aqueous phase as a lower layer including water and the catalyst suspended therein, followed by withdrawing of the oil phase, while recycling the aqueous phase to the reactor.

In the fourth mode of the method of the present invention using a reactor partitioned by means of baffle means, the reaction system also assumes a piston flow through a plurality of chambers arranged in tiers, so that the concentration of produced cyclic alcohol in the oil phase approaches an equilibrium concentration which is generally in the range of between about 10 and about 40% by weight, thereby improving the reaction yield by one pass through the reactor.

In the fourth mode also, a plurality of the reactors may be connected in series as in the third mode of the method of the present invention, so that a reaction yield can be further improved.

PREFERRED EMBODIMENTS OF THE INVENTION

The present invention will now be described in greater detail with reference to the following Examples and Comparative Examples, which should not be construed as limiting the scope of the present invention.

EXAMPLE 1

Cyclohexene is hydrated to produce cyclohexanol by the following method, using as a catalyst H-type ZSM-5 having an average primary particle diameter of 0.04 μm and having a molar ratio of $SiO_2/Al_2O_3$ of 28.

The hydration of cyclohexene is performed in 24-liter cylindrical reactor 4 made of stainless steel and having a configuration as diagrammatically shown in FIG. 1. Reactor 4 has at a lower portion thereof disperser head 6 connected to feed pipe 3 and having a plurality of orifices. Reactor 4 is equipped with a thermometer protecting sheath (not shown) having a thermometer therein (not shown) for measuring the temperature of a reaction system and also with a pressure gauge (not shown) for measuring the pressure in reactor 4. Reactor 4 has at an upper portion thereof an oil phase outlet connected to pipe 5 for withdrawing the oil phase comprised of produced cyclohexanol and unreacted cyclohexene. The above-mentioned feed pipe 3 is connected to pipe 1 for feeding cyclohexene and pipe 2 for feeding water. Feed pipe 3 is also connected to a recycling conduit branched off from oil phase withdrawing pipe 5 so that the withdrawn oil phase is partly recycled to reactor 4 by means of pump 8 and injected from the orifices of disperser head 6. An electric heater (not shown) is attached to the outer surface of reactor 4, and all of the above-mentioned pipes have flow meters (not shown) for measuring the flow rate of a fluid passing therethrough. Disposed in the side wall of cylindrical reactor 4 is a glass peep window (not shown) for observing the separation condition of an oil phase layer from a continuous aqueous phase containing water and oil globules dispersed therein and for determining the position of the interface between the oil phase layer and the continuous aqueous phase.

The hydration reaction of cyclohexene to produce cyclohexanol is carried out according to the following procedure. First, the inside of reactor 4 is purged with nitrogen gas. Then, 19.7 kg of an aqueous slurry containing the above-mentioned catalyst in a concentration of 30% by weight, based on the weight of the slurry, is charged into reactor 4. Immediately thereafter, cyclohexene is introduced into reactor 4 through pipes 1 and 3 and disperser head 6 so that reactor 4, oil phase withdrawing pipe 5, pump 8 and the above-mentioned recycling conduit are filled with a reaction system comprised of the above-mentioned aqueous slurry as an aqueous phase and cyclohexene as an oil phase. Pump 8 is actuated and adjusted so that a recycling is made at a constant flow rate of 600 liters/hr, and that the oil phase in reactor 4 is dispersed in the form of globules. The temperature of the reaction system is elevated to and maintained at 120° C. by means of the electric heater attached to reactor 4, and the internal pressure of reactor 4 is maintained at 6 kg/cm²-gauge by pressurizing with nitrogen gas. Fresh cyclohexene (containing no cyclohexanol) is fed through pipes 1 and at a rate of 6.1 kg/hr under steady operation conditions, and injected from the orifices of disperser head so that the oil phase is dispersed in a continuous phase of the aqueous slurry as globules having an average diameter of 2 mm. Further, water is fed in an amount corresponding to the amount of water which is taken away in a dissolved form in a withdrawn oil phase. Accordingly, the level of the interface between the continuous aqueous phase containing water and oil globules dispersed therein and a continuous oil phase layer, formed in an upper portion of reactor 4 due to unification of oil globules obtained by the hydration reaction, is maintained at a level just below the position of the above-mentioned oil phase outlet connected to oil phase withdrawing pipe 5. The withdrawal of the oil phase from the continuous oil phase layer is controlled so that the level of the interface between the continuous oil phase layer and the gas phase present in a space defined by the continuous oil phase layer and the wall of reactor 4 is maintained at a level above the position of the above-mentioned oil phase outlet. The volume percentage of the oil phase as globules in the reaction system is 10.5%, based on the volume of the continuous aqueous phase. After the entire reaction system has become steady, the oil phase withdrawn through pipe 5 is sampled and its composition is analyzed. The analysis shows that the concentration of cyclohexanol in the withdrawn oil phase is 11.0% by weight and that the selectivity for cyclohexanol is 99.5%. The obtained values are the results of the reaction performed under the reaction rate-limiting conditions, and are found to be satisfactory. The separation of the oil phase from the continuous aqueous phase is good, with no catalyst present in the oil phase withdrawn through oil phase withdrawing pipe 5.

In order to measure the time required for the separation of the oil phase from the continuous aqueous phase, the feeding of cyclohexene and water and the recycling of the oil phase are simultaneously and temporarily stopped. 26 seconds after the stopping of the feeding and recycling, a continuous oil phase layer is formed as an upper layer and a continuous aqueous phase as a lower layer, with no oil globules present in the boundary between the two phases.

EXAMPLE 2 TO 4

Using the same reactor as in Example 1, hydration reactions are performed under substantially the same reaction conditions as in Example 1, except that only the recycling flow rate is varied as indicated in Table 1. The results of the hydration reactions performed are shown in Table 1. The separation of the oil phase from the continuous aqueous phase is good, with no catalyst present in the oil phase withdrawn through oil phase withdrawing pipe 5.

COMPARATIVE EXAMPLE 1

Using the same reactor as in Example 1, a hydration reaction is performed under substantially the same reaction conditions as in Example 1, except that disperser head 6 connected to feed pipe 3 is removed from reactor 4 so that cyclohexene can be injected into reactor 4 directly from feed pipe 3, and that a recycling is conducted at a flow rate of 200 liters/hr. The composition of the oil phase withdrawn through oil phase withdrawing pipe 5 is analyzed. The analysis shows that the concentration of cyclohexanol in the withdrawn oil phase fluctuates over the range of from 1 to 3% by weight and that the selectivity for cyclohexanol is 98.5%. The oil globules dispersed in the continuous aqueous phase have an average diameter of 40 mm.

The results obtained in Comparative Example 1 are shown in Table 1 together with those of Examples 1 to 4.

with a pressure gauge (not shown) for measuring the pressure in reactor 4. Reactor 4 has at an upper portion thereof an oil phase outlet connected to pipe 5 for withdrawing the oil phase comprised of produced cyclohexanol and unreacted cyclohexene. The above mentioned feed pipe 3 is connected to pipe 1 for feeding cyclohexene and pipe 2 for feeding water. The agitating blades of agitator 9 consists of a single set of propeller blades arranged in a common plane. The agitating blades are disposed just above disperser head 6 connected to feed pipe 3. Weir 7 extending from above a gas-liquid free surface (i.e., the interface between the liquid phase and the gas phase present in a space defined by the upper surface of the liquid phase and the upper inner wall of reactor 4) to below the free surface is disposed around the oil phase outlet connected to pipe 5 for providing a stationary zone, to thereby facilitate separation of a reaction mixture obtained by the reaction into an upper oil phase layer comprising produced cyclohexanol and a lower aqueous phase layer comprising water and the catalyst suspended therein. An electric heater (not

TABLE 1

| Example and Comparative Example Nos. | Example 1 | Example 2 | Example 3 | Example 4 | Comparative Example 1 |
| --- | --- | --- | --- | --- | --- |
| Type of reactor | Fig. 1 | Fig. 1 | Fig. 1 | Fig. 1 | Fig. 1 |
| Capacity of the reactor (liters) | 24 | 24 | 24 | 24 | 24 |
| Amount of aqueous slurry containing 30% by weight of catalyst (kg) | 19.7 | 19.7 | 19.7 | 19.7 | 19.7 |
| Feed rate of cyclohexene (kg/hr) | 6.1 | 6.1 | 6.1 | 6.1 | 6.1 |
| Recycling rate (liters/hr) | 600 | 30 | 300 | 900 | 200 |
| Temperature of the reaction system (°C.) | 120 | 120 | 120 | 120 | 120 |
| Internal pressure of the reactor (kg/cm$^2$-gauge) | 6 | 6 | 6 | 6 | 6 |
| Volume ratio (oil phase/continuous aqueous phase) | 0.105 | 0.008 | 0.05 | 0.15 | 0.002 |
| Average diameter of oil globules (mm) | 2 | 5 | 3 | 1.4 | 40 |
| Contact time (min) | 12 | 1.6 | 6.4 | 18 | 0.3 |
| Concentration of cyclohexanol in the withdrawn oil phase (%) | 11.0 | 10.3 | 10.9 | 11.3 | 1–3 (fluctuation) |
| Selectivity for cyclohexanol (%) | 99.5 | 99.4 | 99.5 | 99.5 | 98.5 |
| Time required for the oil phase-continuous aqueous phase separation (sec) | 26 | 19 | 23 | 27 | not measured |

EXAMPLE 5

The hydration of cyclohexene is performed in 4-liter autoclave reactor 4 made of stainless steel and having a configuration as diagrammatically shown in FIG. 2. Reactor 4 is equipped with agitator 9. Disposed in the side wall of reactor 4 is a glass peep window (not shown) for observing an internal state of the reactor. Autoclave reactor 4 has at a lower portion thereof disperser head 6 connected to feed pipe 3 and having a plurality of orifices, disperser head 6 being of the same type as that used in Example 1. Further, reactor 4 is equipped with a thermometer protecting sheath (not shown) having a thermometer therein (not shown) for measuring the temperature of a reaction system and also shown) is attached to the outer surface of reactor 4 for regulation of the reactor temperature. All of the above-mentioned pipes have flow meters (not shown) for measuring the flow rate of fluid passed therethrough. Reactor 4 has four baffle plates (not shown) substantially centripetally projecting from the inner side wall of the reactor.

The hydration reaction of cyclohexene to produce cyclohexanol is carried out according to the following procedure. First, the inside of reactor 4 is purged with nitrogen gas. Then, 2.68 kg of an aqueous slurry containing a fresh catalyst of the same type as used in Example 1, in a concentration of 30% by weight, based on the weight of the slurry, is charged into reactor 4.

The agitator is operated at 530 rpm to agitate the slurry. The temperature of the reaction system (slurry) is elevated to and maintained at 120° C. by means of the electric heater attached to reactor 4. Cyclohexene is gradually fed at start-up through pipes 1 and 3 and disperser head 6, and then at a flow rate of 0.85 kg/hr under steady operation conditions. The internal pressure of reactor 4 is maintained at 6 $kg/cm^2$-gauge under steady operation conditions by pressurizing with nitrogen gas. The level of the interface between the continuous aqueous phase containing water and oil globules dispersed therein and a continuous oil phase layer in the stationary zone in the reactor, is adjusted so that the interface is maintained at a level lower than the position of the oil phase outlet connected to pipe 5. Water is fed through pipe 2 in an amount corresponding to the amount of water which is taken away in a dissolved form in a withdrawn oil phase. The gas-liquid interface (free surface) level is kept constant by adopting an overflow-type pipe as oil phase withdrawing pipe 5. The volume percentage of the oil phase as globules in the reaction system is 30%, based on the volume of the continuous aqueous phase. After the entire reaction system has become steady, the oil phase withdrawn through pipe 5 is sampled and its composition is analyzed. The analysis shows that the concentration of cyclohexanol in the oil phase is 11.1% by weight and that the selectivity for cyclohexanol is 99.5%. The obtained values are the results of the reaction performed under the reaction rate-limiting conditions, and are found to be satisfactory. The agitating power is about 0.5 $kW/m^3$ (The volume being the volume of the entire reaction system). The oil globules in the aqueous phase in reactor 4 have an average diameter of 0.22 mm. The separation of the oil phase from the continuous aqueous phase in the stationary zone is good, with no catalyst present in the oil phase withdrawn through oil phase withdrawing pipe 5.

In order to measure the time required for the separation of the oil phase from the continuous aqueous phase, the feeding of cyclohexene and water and the agitation of the reaction system are simultaneously and temporarily stopped. 12 seconds after the stopping of the feeding and agitation, a continuous oil phase layer is formed as an upper layer and a continuous aqueous phase as a lower layer, with no oil globules present in the boundary between the two phases.

The hydration reaction is restarted and continued for 50 hours under substantially the same reaction conditions as described above. The oil phase withdrawn through pipe 5 is analyzed. As a result, it is found that the concentration of cyclohexanol in the withdrawn oil phase is 10.8% by weight and that the selectivity for cyclohexanol is 99.5%. Almost no lowering of the activity of the catalyst is observed. No catalyst is present in the oil phase withdrawn from pipe 5. When 50 hours have elapsed after the restart of the reaction, the time required for the separation of the oil phase from the continuous aqueous phase is measured in substantially the same manner as described above. 13 seconds after stopping the agitation and feeding, the dispersed oil phase (globules) has completely disappeared. From the above results, it is found that the hydration reaction can be stably conducted during a long period of time.

EXAMPLES 6 to 8

Using the same hydration reactor as in Example 5, hydration reactions are individually carried out under substantially the same reaction conditions as in Example 5, except that only the revolution rate of the agitator is varied as indicated in Table 2. After completion of the reaction, the composition of the oil phase withdrawn through pipe 5 is analyzed. The obtained results are shown in Table 2. The separation of the oil phase from the continuous aqueous phase is good, with no catalyst present in the oil phase withdrawn through pipe 5.

COMPARATIVE EXAMPLE 2

Using the same reactor as in Example 5, a hydration reaction is performed under substantially the same reaction conditions as in Example 5, except that the agitator is operated at 310 rpm instead of 530 rpm. The analysis of the composition of an oil phase withdrawn through pipe 5 shows that the concentration of cyclohexanol in the oil phase is in the range of from 1 to 2% by weight and that the selectivity for cyclohexanol is 98.0%. With respect to the dispersion state observed during the agitation, it is found that a continuous oil phase is present as an upper layer. That is, the oil phase and the continuous aqueous phase are completely separated, and almost no dispersed oil globules are observed in the boundary between the two phases.

The results obtained in Comparative Example 2 are shown in Table 2 together with those of Examples 5 to 8.

TABLE 2

| Example and Comparative Example Nos. | Example 5 | Example 6 | Example 7 | Example 8 | Comparative Example 2 |
|---|---|---|---|---|---|
| Type of reactor | Fig. 2 | Fig. 2 | Fig. 2 | Fig. 2 | Fig. 2 |
| Capacity of the reactor (liters) | 4 | 4 | 4 | 4 | 4 |
| Amount of aqueous slurry containing 30% by weight of catalyst (kg) | 2.68 | 2.68 | 2.68 | 2.68 | 2.68 |
| Feed rate of cyclohexene (kg/hr) | 0.85 | 0.85 | 0.85 | 0.85 | 0.85 |
| Temperature of the reaction system (°C.) | 120 | 120 | 120 | 120 | 120 |
| Internal pressure of the reactor ($kg/cm^2$-gauge) | 6 | 6 | 6 | 6 | 6 |
| Revolution rate of the agitator (rpm) | 530 | 400 | 450 | 700 | 310 |
| Agitating power ($kW/m^3$) | 0.5 | 0.21 | 0.31 | 1.15 | 0.1 |

TABLE 2-continued

| Example and Comparative Example Nos. | Example 5 | Example 6 | Example 7 | Example 8 | Comparative Example 2 |
|---|---|---|---|---|---|
| Volume ratio (oil phase/continuous aqueous phase) | 0.30 | 0.30 | 0.30 | 0.30 | 0.30 |
| Average diameter of oil globules (mm) | 0.22 | 0.35 | 0.3 | 0.15 | * |
| Contact time (min) | 37 | 37 | 37 | 37 | ** |
| Concentration of cyclohexanol in the withdrawn oil phase (%) | *** 11.1 →10.8 | 8.1 | 10.2 | 11.1 | 1–2 (fluctuation) |
| Selectivity for cyclohexanol (%) | 99.5 | 99.0 | 99.4 | 99.5 | 98.0 |
| Time required for the oil phase-continuous aqueous phase separation (sec) | *** 12 → 13 | 7 | 8 | 20 | not measured |

Note:
* The oil phase is not dispersed and forms a continuous layer in the upper portion of the reaction system.
** Due to the separation of the oil phase and the aqueous phase, the interfacial area between the oil phase and the aqueous phase becomes too small, so that the contact time cannot be measured.
*** The arrow means a change in value after 50 hours of reaction.

EXAMPLE 9

Autoclave reactor 4 as shown in FIG. 3 is employed, which has hollow cylinder (draft tube) 10 disposed therein having an inner and an outer wall and a top and a bottom open end to enclose the agitator, providing a first spacing between the agitator and the inner wall of cylinder 10 within the reaction system in reactor 4 and providing a second spacing between the outer wall of cylinder 10 and the inner wall of reactor 4 within the reaction system in reactor 4. The over-flow-type outlet for withdrawing the oil phase (which is connected to pipe 5) is disposed at a position which is slightly above the position of the oil phase outlet in Example 5. Reactor 4 is of the same structure as that employed in Example 5 except that as described above, it has a draft tube and the position of the oil phase withdrawing outlet is slightly higher than in Example 5. A fresh catalyst of the same type as used in Example 1, is employed.

A hydration reaction is carried out under substantially the same reaction conditions as in Example 5. After the entire reaction system has become steady, the composition of the oil phase withdrawn through pipe 5 is analyzed. The analysis shows that the concentration of cyclohexanol in the withdrawn oil phase is 11.2% by weight and that the selectivity for cyclohexanol is 99.5%. The separation of the oil phase from the continuous aqueous phase is good, with no catalyst present in the oil phase withdrawn through pipe 5.

In order to measure the time required for the separation of the oil phase from the continuous aqueous phase, the feeding of cyclohexene and water and the agitation of the reaction system are simultaneously and temporarily stopped. 11 seconds after the stopping of the feeding and agitation, a continuous oil phase layer is formed as an upper layer and a continuous aqueous phase is formed as a lower layer, with no oil globules present in the boundary between the two phases. The volume percentage of the oil phase in the reaction system is 40%.

EXAMPLE 10 to 12

Using the same reactor as in Example 9, hydration reactions are individually carried out under substantially the same reaction conditions as in Example 9, except that the revolution rate of the agitator is varied as indicated in Table 3. The separation of the oil phase from the continuous aqueous phase is good, with no catalyst present in the oil phase withdrawn through pipe 5. It is found that by virtue of the use of a hollow cylinder (draft tube) disposed within the reactor, even when the revolution rate of the agitator is lowered, the concentration of cyclohexanol in the withdrawn oil phase can be kept at a high level.

COMPARATIVE EXAMPLE 3

Using the same reactor as in Example 9, a hydration reaction is performed under substantially the same reaction conditions as in Example 9, except that the revolution rate of the agitator is lowered to 50 rpm. After the entire reaction system has become steady, the composition of the oil phase withdrawn through pipe 5 is analyzed. The analysis shows that the concentration of cyclohexanol in the withdrawn oil phase is in the range of from 1 to 2% by weight and that the selectivity for cyclohexanol is 97.8%. It is found that during the reaction, a continuous oil phase is present in the upper layer of the reaction system. That is, the oil phase and the aqueous phase are completely separated, and almost no dispersed oil phase (globules) is observed.

Reaction conditions and results of Examples 9 to 12 and Comparative Example 3 are summarized in Table 3 below.

TABLE 3

| Example and Comparative Example Nos. | Example 9 | Example 10 | Example 11 | Example 12 | Comparative Example 3 |
|---|---|---|---|---|---|
| Type of reactor | Fig. 3 | Fig. 3 | Fig. 3 | Fig. 3 | Fig. 3 |
| Capacity of the reactor (liters) | 4 | 4 | 4 | 4 | 4 |
| Amount of aqueous | 2.68 | 2.68 | 2.68 | 2.68 | 2.68 |

TABLE 3-continued

| Example and Comparative Example Nos. | Example 9 | Example 10 | Example 11 | Example 12 | Comparative Example 3 |
|---|---|---|---|---|---|
| slurry containing 30% by weight of catalyst (kg) | | | | | |
| Feed rate of cyclohexene (kg/hr) | 0.85 | 0.85 | 0.85 | 0.85 | 0.85 |
| Temperature of the reaction system (°C.) | 120 | 120 | 120 | 120 | 120 |
| Internal pressure of the reactor (kg/cm$^2$-gauge) | 6 | 6 | 6 | 6 | 6 |
| Revolution rate of the agitator (rpm) | 530 | 250 | 300 | 350 | 50 |
| Agitating power (kW/m$^3$) | 0.46 | 0.051 | 0.088 | 0.14 | ≦0.01 |
| Volume ratio (oil phase/continuous aqueous phase) | 0.4 | 0.4 | 0.4 | 0.4 | 0.4 |
| Average diameter of oil globules (mm) | 0.26 | 0.7 | 0.5 | 0.4 | * |
| Contact time (min) | 48 | 48 | 48 | 48 | ** |
| Concentration of cyclohexanol in the withdrawn oil phase (%) | 11.2 | 10.3 | 10.7 | 11.0 | 1–2 (fluctuation) |
| Selectivity for cyclohexanol (%) | 99.5 | 99.4 | 99.5 | 99.5 | 97.8 |
| Time required for the oil phase-continuous aqueous phase separation (sec) | 11 | 4 | 4 | 4 | not measured |

Note:
* The oil phase is not dispersed and forms a continuous layer in the upper portion of the reaction system.
** Due to the separation of the oil phase and the aqueous phase, the interfacial area between the oil phase and the aqueous phase becomes too small, so that the contact time cannot be measured.

EXAMPLE 13

Autoclave reactor 4 as shown in FIG. 4 is employed, which is connected, through pipe 12 for withdrawing a reaction mixture, to 1-liter oil phase-aqueous phase separator 11 having a cone-shaped bottom. Oil phase-aqueous phase separator 11 is designed so that the oil phase of the reaction mixture introduced thereto is separated as an upper layer containing a produced cyclic alcohol from the continuous aqueous phase as a lower layer comprising the water and the catalyst suspended therein. The oil phase is withdrawn through pipe 5 (the oil phase being partly recycled to reactor 4), and the aqueous phase is recycled to reactor 4 through pipe 13 provided at the bottom of oil phase-aqueous phase separator 11. Oil phase-aqueous phase separator 11 has a glass peep window (not shown) for determining the position of the interface between the oil phase and the continuous aqueous phase. The withdrawal of the oil phase from oil phase-aqueous phase separator 11 is controlled so that the gas-liquid interface (free surface) levels in both of the reactor and the oil phase-aqueous phase separator are stably maintained at substantially the same level relative to each other. Reactor 4 is of the same structure as that of the reactor used in Example 9 except that the above modifications are made (for providing an oil phase-aqueous phase separator outside of the reactor instead of a stationary zone within the reactor) and that a draft tube is not used.

A part of the oil phase withdrawn from oil phase-aqueous phase separator 11 through pipe 5 is recycled to feed pipe 3 at a flow rate of 20 liters/hr by means of pump 8. The agitator is operated at 100 rpm and the agitating power is 0.01 kW/m$^3$.

A hydration reaction is carried out in substantially the same manner as in Example 9. After the entire reaction system has become steady, the composition of the oil phase withdrawn through pipe 5 is analyzed. The analysis shows that the concentration of cyclohexanol in the withdrawn oil phase is 11.2% by weight and that the selectivity for cyclohexanol is 99.5%, which are the same results as in Example 9. The separation of the oil phase from the aqueous phase is good, with no catalyst present in the oil phase withdrawn through pipe 5.

In order to measure the time required for the separation of the oil phase from the continuous aqueous phase, the feeding of the cyclohexene and water, the agitation of the reaction system, and the recycling of the oil phase are simultaneously and temporarily stopped. The time required for the separation is 4 seconds.

EXAMPLE 14

Using the same reactor as in Example 5, a hydration reaction is carried out under substantially the same reaction conditions as in Example 5, except that cyclopentene is used instead of cyclohexene as a feedstock. After the entire reaction system has become steady, the composition of the oil phase is withdrawn through pipe 5 is analyzed. The analysis shows that the concentration of cyclopentanol in the withdrawn oil phase is 7.1% by weight and that the selectivity for cyclopentanol is 99.5%, which are good results. The separation of the oil phase from the continuous aqueous phase is good, with no catalyst present in the oil phase withdrawn from pipe 5.

In order to measure the time required for the separation of the oil phase from the continuous aqueous phase, the feeding of cyclopentene and water and the agitation of the reaction system are simultaneously and temporarily stopped. The time required for the separation is 13 seconds.

EXAMPLE 15

Autoclave reactor 4 as shown in FIG. 5 is employed, in which partition member 7A for partitioning the inside of reactor 4 into an agitation zone as a lower zone and a stationary zone as an upper zone, is disposed at an upper portion of reactor 4. Reactor 4 is of the same structure as that used in Example 5 except that the above modification is made. A fresh catalyst of the same type as used in Example 1 is employed.

A hydration reaction is carried out under substantially the same reaction conditions as in Example 5. After the reaction system has become steady, the composition of the oil phase withdrawn through pipe 5 is analyzed. The analysis shows that the concentration of cyclohexanol in the withdrawn oil phase is 11.0% by weight and that the selectivity for cyclohexanol is 99.5%. The separation of the oil phase from the aqueous phase is good, with no catalyst present in the oil phase withdrawn from pipe 5.

In order to measure the time required for the separation of the oil phase from the continuous aqueous phase, the feeding of cyclohexene and water and the agitation of the reaction system are simultaneously and temporarily stopped. The time required for the separation is 11 seconds.

COMPARATIVE EXAMPLE 4

Using the same reactor as in Example 5, a hydration reaction is carried out under substantially the same reaction conditions as in Example 5, except that the revolution rate of the agitator is 1000 rpm instead of 530 rpm. As a result, it is found that a part of the catalyst is contained in the oil phase withdrawn through pipe 5, indicating that the separation of the oil phase from the continuous aqueous phase is not good. The concentration of cyclohexanol in the oil phase withdrawn through pipe 5 is 10.9% by weight and the selectivity for cyclohexanol is 99.5%. The oil globules in the reaction system have an average diameter of 0.03 mm.

In order to measure the time required for the separation of the oil phase from the aqueous phase, the feeding of cyclohexene and water and the agitation of the reaction system are simultaneously and temporarily stopped. Even 74 seconds after the stopping of the feeding and the agitation, an emulsion layer remains between the continuous oil phase layer and the continuous aqueous phase layer.

The hydration reaction is restarted and continued for 50 hours under the same reaction conditions as employed above. After that period, the composition of the oil phase withdrawn through pipe 5 is analyzed. The analysis shows that the concentration of cyclohexanol in the withdrawn oil phase has decreased to 8.5% by weight.

During the reaction, the withdrawn oil phase containing the emulsion (which contains water having the catalyst suspended therein) is subjected to centrifugation to thereby effect separation between the oil phase and the aqueous phase. The thus separated aqueous phase, containing the catalyst which has leaked out from reactor 4, is recycled to reactor 4 through a spare nozzle (not shown) so that during the reaction the amount of the catalyst within the reaction system is maintained at substantially the same level as that of the amount of the initially charged catalyst.

Reaction conditions and results of Examples 13 to 15 and Comparative Example 4 are shown in Table 4.

TABLE 4

| Example and Comparative Example Nos. | Example 13 | Example 14 | Example 15 | Comparative Example 4 |
| --- | --- | --- | --- | --- |
| Type of reactor | Fig. 4 | Fig. 2 | Fig. 5 | Fig. 2 |
| Capacity of the reactor (liters) | 4 | 4 | 4 | 4 |
| Amount of aqueous slurry containing 30% by weight of catalyst (kg) | 3.5 | 2.68 | 2.68 | 2.68 |
| Feed rate of cyclohexene (kg/hr) | 0.85 | 0.85 *** | 0.85 | 0.85 |
| Recycling rate (liters/hr) | 20 | — | — | — |
| Temperature of the reaction system (°C.) | 120 | 120 | 120 | 120 |
| Internal pressure of the reactor (kg/cm$^2$-gauge) | 6 | 6 | 6 | 6 |
| Revolution rate of the agitator (rpm) | 100 | 530 | 530 | 1000 |
| Agitation power (kW/m$^3$) | 0.01 | 0.5 | 0.57 | 3.4 |
| Volume ratio (oil phase/continuous aqueous phase) | 0.3 | 0.3 | 0.15 | 0.3 |
| Average diameter of oil globules (mm) | 1.5 | 0.25 | 0.2 | 0.03 |
| Contact time (min) | 37 | 37 | 19 | 37 * |
| Concentration of cyclohexanol in the withdrawn oil phase (%) | 11.2 | 7.1 | 11.0 | 10.9 → 8.5 |
| Selectivity for cyclohexanol (%) | 99.5 | 99.5 | 99.5 | 99.5 |

TABLE 4-continued

| Example and Comparative Example Nos. | Example 13 | Example 14 | Example 15 | Comparative Example 4 |
|---|---|---|---|---|
| Time required for the oil phase-continuous aqueous phase separation (sec) | 4 | 13 | 11 | 74 ** |

* Arrow means a change in concentration of cyclohexanol after 50 hours of reaction.
** After 74 seconds, an emulsion layer still reamains.
*** Cyclopentene is used instead of cyclohexene.

EXAMPLE 16

The hydration reaction of cyclohexene to produce cyclohexanol is carried out according to the following method.

For the hydration reaction, two autoclave reactors 4-1 and 4-2 shown in FIG. 7 are employed, which are pressure vessels of the same type as used in Example 5. Reactors 4-1 and 4-2, each having a capacity of 4 liters, are made of stainless steel. As is diagrammatically shown in FIG. 7, reactors 4-1 and 4-2 are connected in series. Reactor 4-2 as a second reactor is positioned lower than reactor 4-1 as a first reactor. A reaction mixture, which is obtained in the first reactor 4-1 and comprises produced cyclohexanol and unreacted cyclohexene, is introduced to the second reactor 4-2 to thereby hydrate the unreacted cyclohexene. Pipe 5-1 for withdrawing an oil phase from the first reactor 4-1 is connected to feed pipe 3 leading to the second reactor 4-2. The first reactor and second reactor are communicated with each other through pipe 18 for pressure equalization between the first reactor and the second reactor. Pipe 19 for supplying an inert gas for pressurization is connected to pressure equalizing pipe 18. The first reactor has a coil-shaped conduit for passing steam for heating, and the coil-shaped conduit has steam inlet 14 and steam outlet 15, while the second reactor has a coil-shaped conduit for passing steam or cooling water and the coil conduit has its inlet 16 and outlet 17 for steam or cooling water, thereby enabling the regulation of the internal temperatures of the reactors.

The hydration reaction of cyclohexene to produce cyclohexanol is carried out according to the following procedure. First, the inside of each reactor is purged with nitrogen gas. Then, 5.36 kg of an aqueous slurry containing a fresh catalyst of the same type as used in Example 1, in a concentration of 30% by weight, based on the weight of the aqueous slurry, is charged into each reactor. The agitators of the first and second reactors are operated at 530 rpm to agitate the slurries, and the internal temperatures of the first and second reactors are elevated to and maintained at 120° C. by passing steam for heating through the coil-shaped conduits. Fresh cyclohexene is fed gradually at start-up and then at a flow rate of 1.7 kg/hr under steady operation conditions. The internal pressure of the reactors is maintained at 7 kg/cm²-gauge under steady operation conditions by pressurizing with nitrogen gas. The level of the interface between the continuous aqueous phase and the continuous oil phase in the stationary zones in each reactor is adjusted so that the interface is maintained at a level lower than the position of the oil phase outlet connected to pipe 5-1 for reactor 4-1 or pipe 5-2 for reactor 4-2. Water is fed through pipes 2, 2 in an amount corresponding to the amount of water which is taken away in a dissolved form in oil phases withdrawn through pipes 5-1 and 5-2. The gas-liquid free surface level in each reactor is kept constant by adopting an overflow-type pipe as each of oil phase withdrawing pipes 5-1 and 5-2. With respect to the second reactor containing a coil-shaped conduit having its inlet 16 and outlet 17 for steam or cooling water, maintenance of the internal temperature thereof at a constant temperature of 120° C. is conducted by passing steam through the conduit initially and then shifting to cooling water. After the entire reaction system has become steady, the composition of the oil phase withdrawn through pipe 5-2 is analyzed. The analysis shows that the concentration of cyclohexanol in the withdrawn oil phase is 12.2% by weight and that the selectivity for cyclohexanol is 99.5%. The agitating power used to agitate the reaction system is about 0.5 kW/m³. Though the amount of fed cyclohexene per unit weight the catalyst is the same as in Example 5, it is found that the concentration of cyclohexanol in the withdrawn oil phase through pipe 5-2 shows an increase of about 10% over in Example 5. The separation of the oil phase from the aqueous phase is good, with no catalyst present in the oil phase withdrawn through pipe 5-2.

EXAMPLES 17 AND 18

Using the same reactor as in Example 16, hydration reactions are individually performed under substantially the same reaction conditions as in Example 16, except that only the temperature of the reaction system in the second reactor is varied as indicated in Table 5. The results of the hydration reactions performed are shown in Table 5.

COMPARATIVE EXAMPLE 5

Using the same reactor as in Example 16, a hydration reaction is conducted under substantially the same reaction conditions as in Example 16, except that the temperature of the reaction system in the second reactor is maintained at 130° C. (which is 10° C. higher than in the first reactor) After completion of the reaction, the composition of the oil phase withdrawn through pipe 5-2 is analyzed. The analysis shows that the concentration of cyclohexanol in the withdrawn oil phase is 9.2% by weight and that the selectivity for cyclohexanol is 99.3%. It is found that the concentration of cyclohexanol in the oil phase withdrawn through pipe 5-2 shows a decrease of about 25% relative to that in Example 16 in which the reaction temperature is 120° C. in both of the first and second reactors.

The results obtained in Comparative Example 5 are shown in Table 5 together with those of Examples 16 to 18.

TABLE 5

| Example and Comparative Example Nos. | Example 16 | Example 17 | Example 18 | Comparative Example 5 |
|---|---|---|---|---|
| Type of reactor | Fig. 7 | Fig. 7 | Fig. 7 | Fig. 7 |
| Capacity of each of the reactors (liters) | 4 | 4 | 4 | 4 |
| Amount of aqueous slurry containing 30% by weight of catalyst (kg) | 5.36 | 5.36 | 5.36 | 5.36 |
| Feed rate of cyclohexene (kg/hr) | 1.7 | 1.7 | 1.7 | 1.7 |
| Temperature of the reaction system (°C.) | *<br>120/120 | *<br>120/115 | *<br>120/110 | *<br>120/130 |
| Internal pressure of the reactor (kg/cm$^2$-gauge) | 7 | 7 | 7 | 7 |
| Revolution rate of the agitator (rpm) | 530 | 530 | 530 | 530 |
| Agitating power (kW/m$^3$) | 0.5 | 0.5 | 0.5 | 0.5 |
| Volume ratio (oil phase/continuous aqueous phase) | 0.3 | 0.3 | 0.3 | 0.3 |
| Average diameter of oil globules (mm) | 0.2 | 0.2 | 0.2 | 0.2 |
| Contact time (min) | 37 | 37 | 37 | 37 |
| Concentration of cyclohexanol in the withdrawn oil phase (%) | 12.2 | 14.5 | 15.5 | 9.2 |
| Selectivity for cyclohexanol (%) | 99.5 | 99.6 | 99.6 | 99.3 |
| Time required for the oil phase-continuous aqueous phase separation (sec) | 13 | 13 | 13 | 13 |

* Values shown in the left and right sides of slash (/) are, respectively, the temperatures of the reaction systems in the first and second reactors.

EXAMPLE 19

As a reactor for the hydration reaction of cyclohexene to produce cyclohexanol, a 32-liter cylindrical autoclave reactor 4 made of stainless steel and having a configuration as diagrammatically shown in FIG. 8 is employed. Reactor 4 has at a lower portion thereof disperser head 6 connected to feed pipe 3 and having a plurality of orifices. Reactor 4 is equipped with a thermometer protecting sheath (not shown) having a thermometer therein (not shown) for measuring the temperature of a reaction system, a gas-liquid interface level meter (not shown), a liquid-liquid interface level meter (not shown) and a pressure gauge (not shown) for measuring the pressure in reactor 4. Reactor 4 has at an upper portion thereof an oil phase outlet connected to pipe 5 for withdrawing the oil phase comprised of produced cyclohexanol and unreacted cyclohexene. The above-mentioned feed pipe 3 is connected to pipe 1 for feeding cyclohexene and pipe 2 for feeding water Pipes 1 to 3 have their respective flowmeters. Agitator 9 consists of 10-step type disk turbine blades including 10 blade sets arranged in tiers. The lowermost blade set is disposed just above disperser head 6. Reactor 4 is partitioned by means of baffle means 20 [of the same type as that of baffle means 20A shown in FIG. 9(a)] having a perforation ratio of 14%, to separate reactor 4 into 10 chambers arranged in tiers, and each chamber contains one blade set. Reactor 4 has, at a position between the oil phase outlet and the uppermost blade set 9, another baffle means 20 of the same type as those disposed below so that the zone positioned around the oil phase outlet and above the additional uppermost baffle means 20 serves as a stationary zone to facilitate separation of an oil phase from a continuous aqueous phase.

Further, reactor 4 has steam jacket 21 on the periphery of the lowermost chamber containing the lowermost blade set, for regulating the internal temperature of the chamber. Steam jacket 21 is connected to supply pipe 14 having a valve for controlling the flow rate of steam and to withdrawing pipe 15. Also, each of the remaining chambers from the second (from bottom) through the tenth chambers has cooling water jacket 22 on its periphery for regulating the internal temperature of each chamber. Each cooling water jacket 22 is connected to supply pipe 16 having a valve for controlling the flow rate of cooling water and connected to withdrawing pipe 17.

The hydration reaction of cyclohexene to produce cyclohexanol is carried out according to the following procedure. First, the inside of reactor 4 is purged with nitrogen gas. Then, 19.7 kg of an aqueous slurry containing a fresh catalyst of the same type as used in Example 1, in a concentration of 30% by weight, based on the weight of the slurry, is charged into reactor 4. The agitator 9 is operated at 350 rpm to agitate the slurry. The temperature of the reaction system (slurry) is elevated to and maintained at 120° C. by passing steam through the steam jacket 21 attached to the reactor The internal pressure of reactor 4 is maintained at 7 kg/cm$^2$-gauge under steady operation conditions by pressurizing with nitrogen gas. Fresh cyclohexene is fed through pipes 1 and 3 at a rate of 6.1 kg/hr under steady operation conditions, and injected from the orifices of disperser head 6. The temperature of the reaction system is maintained at 120° C. by passing cooling water through jackets 22. The level of the interface between the continuous aqueous phase layer and a continuous oil phase layer in the stationary zone in the reactor, is adjusted so that the interface is maintained at a level lower than the position of the oil phase outlet connected to pipe 5. Water is fed through pipe 2 in an amount corresponding to the amount of water which is taken away in a dissolved form in a withdrawn oil phase. The withdrawal of the oil phase from the continuous oil phase layer is controlled so that the level of the interface between the continuous oil phase layer and the gas phase present in a space defined by the upper surface of the continuous oil phase layer and the upper inner wall of reactor 4 is maintained at a level above the position of the above-mentioned oil phase outlet. After the entire reaction system has become steady, the composition of the oil phase withdrawn through pipe 5 is analyzed. The analysis shows that the concentration of cyclohexanol is 13.0% by weight and that the selectivity for cyclohexanol is 99.5%. Though the amount of fed cyclohexene per unit weight of the catalyst is the same as in Example 5, it is found that the concentration of cyclohexanol in the withdrawn oil phase is higher than in Example 5, by virtue of the structure of reactor 4 in which a plurality of chambers as independent agitation zones are arranged in tiers. The separation of the oil phase from the aqueous phase is good, with no catalyst present in the oil phase withdrawn through pipe 5.

EXAMPLE 20

Using the same reactor as in Example 19, a hydration reaction of cyclohexene to produce cyclohexanol is conducted under substantially the same reaction conditions as in Example 19, except that the temperatures of the chambers are controlled so as to be successively lowered from 120° to 105° C. in the direction of flow of the reaction system through the chambers. With respect to the regulation of the temperatures of the chambers, the lowermost chamber is maintained at a temperature of 120° C. and the uppermost chamber is maintained at a temperature of 105° C., and the chambers successively disposed between the lowermost and uppermost chambers are maintained at predetermined temperatures so that an approximately linear temperature distribution over the range of 120° to 105° C. is produced in the reaction system through the chambers. After the entire reaction system has become steady, the composition of the oil phase withdrawn through pipe 5 is analyzed. The analysis shows that the concentration of cyclohexanol in the withdrawn oil phase is 15.1% by weight and that the selectivity for cyclohexanol is 99.6%. It is found that the concentration of cyclohexanol in the withdrawn oil phase is higher than in Example 19 in which all of the chambers are maintained at an even temperature. The separation of the oil phase from the aqueous phase is good, with no catalyst present in the oil phase withdrawn through pipe 5.

The results obtained in Examples 19 and 20 are shown in Table 6.

TABLE 6

| Example Nos. | Exampl3 19 | Example 20 |
|---|---|---|
| Type of reactor | Fig. 8 | Fig. 8 |
| Capacity of the reactor (liters) | 32 | 32 |
| Amount of aqueous slurry containing 30% by weight of catalyst (kg) | 19.7 | 19.7 |
| Feed rate of cyclohexene (kg/hr) | 6.1 | 6.1 |
| Temperature of the reaction system (°C.) | 120 | 120 → 105 |
| Internal pressure of the reactor (kg/cm$^2$-gauge) | 7 | 7 |
| Revolution rate of the agitator (rpm) | 350 | 350 |
| Agitating power (kW/m$^3$) | 0.7 | 0.7 |
| Volume ratio (oil phase/continuous aqueous phase) | 0.06 | 0.06 |
| Average diameter of oil globules (mm) | 0.18 | 0.18 |
| Contact time (min) | 7 | 7 |
| Concentration of cyclohexanol in the withdrawn oil phase (%) | 13.0 | 15.1 |
| Selectivity for cyclohexanol (%) | 99.5 | 99.6 |
| Time required for the oil phase-continuous aqueous phase separation (sec) | 30 | 34 |

What is claimed is:

1. A method for hydrating a cycloolefin to produce a cyclic alcohol corresponding thereto, comprising reacting a cycloolefin with water in the presence of a crystalline aluminosilicate catalyst,
    said cycloolefin being selected from the group consisting of cyclopentene, methylcyclopenten, cyclohexene, methylcyclohexene, cyclooctene and cyclododecene,
    said reaction being effected in a reaction system comprising:
    a continuous aqueous phase including water and the crystalline aluminosilicate catalyst suspended therein; and
    an oil phase including the cycloolefin, while dispersing the oil phase in the continuous aqueous phase as globules having an average diameter of between about 0.05 and about 30 mm.

2. The method according to claim 1, wherein said crystalline aluminosilicate catalyst has an average primary particle diameter of about 0.5 μm or less.

3. The method according to claim 1, wherein said volume ratio of said oil phase to said continuous aqueous phase is between about 0.001:1 and about 1.0:1.

4. The method according to claim 1, wherein the weight ratio of said crystalline aluminosilicate catalyst to said water is between about 0.01:1 and about 2.0:1.

5. The method according to claim 1, wherein said oil phase comprises said cycloolefin in an amount of between about 50 and about 100% by weight and a cyclic alcohol corresponding to said cycloolefin in an amount of between 0 and about 50% by weight, based on the weight of the oil phase.

6. The method according to claim 1, wherein said reaction is conducted at a temperature of between about 50° and about 250° C. under a pressure at which said water and cycloolefin are liquid.

7. The method according to claim 1, wherein said reaction is conducted in at least one reactor having at a lower portion thereof at least one disperser head connected to a feed pipe, said disperser head having a plurality of orifices, and wherein said oil phase is fed through said feed pipe and injected from the orifices of said disperser head into the reaction system, thereby dispersing and moving said oil phase in said continuous aqueous phase as the oil globules.

8. The method according to claim 7, wherein said reactor has at an upper portion thereof an oil phase connected to means for withdrawing an oil phase, by the reaction, comprising produced cyclic alcohol and unreacted cycloolefin, and wherein a continuous oil phase layer, formed in an upper portion of the reactor due to unification of oil globules obtained by the reaction, is withdrawn through said outlet and said withdrawing means and partly recycled to the reactor through a recycling conduit branched off from said oil phase withdrawing means and connected to said feed pipe, so that the recycled oil phase is injected from the orifices of said disperser head.

9. The method according to claim 8, wherein the weight ratio of said recycled oil phase to cycloolefin feed is between about 1:1 and about 150:1.

10. The method according to claim 1, wherein said reaction is conducted in at least one reactor having an agitator with a plurality of agitating blades, and wherein said agitator is operated so that the entire reaction system is agitated to produce a shearing force, thereby dispersing the oil phase in the continuous aqueous phase while preventing the catalyst suspended in the continuous aqueous phase from settling and dividing aggregated oil globules, formed in the reaction system at places distant from said agitating blades, into re-dispersed oil globules.

11. The method according to claim 7, wherein said reactor has an agitator with a plurality of agitating blades, and wherein said agitator is operated so that the entire reaction system is agitated to produce a shearing force, thereby dispersing the oil phase in the continuous aqueous phase while preventing the catalyst suspended in the continuous aqueous phase from settling and dividing aggregated oil globules, formed in the reaction system at places distant from said agitating blades, into re-dispersed oil globules.

12. The method according to claim 7, 10 or 11, wherein said reaction is conducted using a plurality of reactors, connected in series, including a first reactor and at least one additional reactor, and wherein a reaction mixture, which is obtained in a reactor preceding said additional reactor and comprises a produced cyclic alcohol and an unreacted cycloolefin, is introduced to said additional reactor to thereby hydrate said unreacted cycloolefin.

13. The method according to claim 10 or 11, wherein said reactor has at an upper portion thereof an outlet for a reaction product as an oil phase, and has a weir around said outlet for providing a stationary zone to thereby facilitate separation of a reaction mixture obtained by said reaction into an upper oil phase layer comprising a produced cyclic alcohol and a lower aqueous phase layer having the catalyst suspended therein.

14. The method according to claim 10 or 11, wherein said reactor is partitioned by means of a partition member to provide an agitation zone as a lower zone and a stationary zone as an upper zone, and wherein the reaction system is agitated in said agitation zone to produce said shearing force so that the oil phase is dispersed in said continuous aqueous phase as the oil globules, while said partition member allows the oil globules to flow from said agitation zone to said stationary zone so that unification of said oil globules occurs in said stationary zone to form a continuous oil phase layer therein.

15. The method according to claim 14, wherein said partition member is selected from the group consisting of a perforated disk, a non-perforated disk, a doughnut plate and a grid deck.

16. The method according to claim 10 or 11, wherein said reactor has, disposed therein, a hollow cylinder having an inner wall and an outer wall and a top and a bottom open end to enclose said agitator, providing a first spacing between the agitator and the inner wall of the cylinder within the reaction system in the reactor and providing a second spacing between the outer wall of the cylinder and the inner wall of the reactor within the reaction system in the reactor, said cylinder having a horizontal cross-section area sufficient to cause the reaction system to be circulated through said first and second spacings within the reactor, so that said cylinder functions as a draft tube.

17. The method according to claim 10 or 11, wherein said reactor has at least one vertically extending baffle plate substantially centripetally projecting from the inner side wall of the reactor and terminating at a position near said side wall, with a spacing remaining above and below said baffle plate within the reaction system.

18. The method according to claim 10 or 11, wherein said plurality of agitating blades include a plurality of blade sets arranged in tiers,
wherein said reactor is partitioned by means of baffle means into a plurality of chambers arranged in tiers so that each chamber contains at least one set of said blade sets, providing independent agitation zones for said reaction system,
wherein said agitator is operated so that the entire reaction system in each chamber is agitated to produce said shearing force, thereby dispersing the oil phase in the continuous aqueous phase while preventing the catalyst suspended in the continuous aqueous phase from settling and dividing aggregated oil globules, formed in said reaction system in each chamber at places distant from said agitating blades, into redispersed oil globules, and
wherein said baffle means allows the reaction system to flow from a first chamber of two mutually adjacent chambers partitioned by said baffle means to a second chamber of said adjacent chambers in accordance with a predetermined direction of flow of the reaction system, while said baffle means prevents flow of the reaction system in a counter direction to said predetermined direction, so that the reaction system in said second chamber is prevented from being back-mixed with the reaction system in said first chamber.

19. The method according to claim 18, wherein the uppermost baffle means provides an agitation zone as a lower zone and a stationary zone as an upper zone, which are, respectively, positioned below and above said uppermost baffle means, and wherein the reaction system is agitated in said agitation zone to produce said shearing force so that the oil phase is dispersed in said continuous aqueous phase as the oil globules, while said baffle means allows the oil globules to flow from said agitation zone to said stationary zone so that unification of said oil globules occurs in said stationary zone to form a continuous oil phase layer therein.

20. The method according to claim 18, wherein the uppermost chamber of said chambers has an outlet for a reaction product as an oil phase, and has a weir around said outlet for providing a stationary zone to thereby facilitate separation of a reaction mixture obtained by said reaction into an upper oil phase layer comprising a produced cyclic alcohol and a lower aqueous phase layer comprising the water and the catalyst suspended therein.

21. The method according to claim 1 or 7, wherein a reaction mixture, obtained by said reaction, comprising an oil phase and an aqueous phase is introduced into an oil phase-aqueous phase separator disposed outside of the reactor to thereby separate the oil phase as an upper layer comprising a produced cyclic alcohol from the aqueous phase as a lower layer comprising the water and the catalyst suspended therein, followed by withdrawal of said oil phase, said oil phase being partly recycled to said reactor, while recycling said aqueous phase to said reactor.

22. The method according to claim 10 or 11, wherein a reaction mixture, obtained by said reaction, comprising an oil phase and an aqueous phase is introduced into an oil phase-aqueous phase separator disposed outside of the reactor to thereby separate the oil phase as an upper layer comprising a produced cyclic alcohol from the aqueous phase as a lower layer comprising the water and the catalyst suspended therein, followed by withdrawal of said oil phase, said oil phase being partly recycled to said reactor, while recycling said aqueous phase to said reactor.

23. The method according to claim 18, wherein a reaction mixture, obtained by said reaction, comprising an oil phase and an aqueous phase is introduced into an oil phase-aqueous phase separator disposed outside of the reactor to thereby separate the oil phase as an upper layer comprising a produce cyclic alcohol from the aqueous phase as a lower layer comprising the water and the catalyst suspended therein, followed by withdrawal of said oil phase, while recycling said aqueous phase to said reactor.

24. The method according to claim 12, wherein the temperatures of said plurality of reactors are controlled so as to be successfully lowered in accordance with a direction of flow of the reaction system through said reactors.

25. The method according to claim 18, wherein the temperatures of said plurality of chambers are controlled so as to be successfully lowered in accordance with a direction of flow of the reaction system through said chambers.

* * * * *